US012605326B2

(12) United States Patent
Joshi et al.

(10) Patent No.: US 12,605,326 B2
(45) Date of Patent: Apr. 21, 2026

(54) COSMETIC COMPOSITION COMPRISING A POLYMER COMPRISING AT LEAST ONE CATIONIC (METH)ACRYLAMIDE UNIT, A PARTICULAR SILICONE AND AT LEAST ONE SURFACTANT

(71) Applicant: L'OREAL, Paris (FR)

(72) Inventors: Sarish Joshi, Mumbai (IN); Kishor Dagwar, Mumbai (IN); Harshada Tulsyan, Mumbai (IN)

(73) Assignee: L'OREAL, Paris (FR)

(*) Notice: Subject to any disclaimer, the term of this patent is extended or adjusted under 35 U.S.C. 154(b) by 698 days.

(21) Appl. No.: 17/788,510

(22) PCT Filed: Dec. 16, 2020

(86) PCT No.: PCT/EP2020/086563

§ 371 (c)(1),
(2) Date: Jun. 23, 2022

(87) PCT Pub. No.: WO2021/130088

PCT Pub. Date: Jul. 1, 2021

(65) Prior Publication Data

US 2023/0065360 A1 Mar. 2, 2023

(30) Foreign Application Priority Data

Dec. 24, 2019 (IN) ............................ 201921053705

(51) Int. Cl.

| | |
|---|---|
| ***A61K 8/81*** | (2006.01) |
| ***A61K 8/06*** | (2006.01) |
| ***A61K 8/894*** | (2006.01) |
| ***A61Q 5/02*** | (2006.01) |
| ***A61Q 5/12*** | (2006.01) |

(52) U.S. Cl.

CPC ............ *A61K 8/8158* (2013.01); *A61K 8/062* (2013.01); *A61K 8/894* (2013.01); *A61Q 5/02* (2013.01); *A61Q 5/12* (2013.01); *A61K 2800/21* (2013.01); *A61K 2800/432* (2013.01)

(58) Field of Classification Search

CPC ...... A61K 8/8158; A61K 8/062; A61K 8/894; A61K 2800/21; A61K 2800/432; A61K 8/86; A61K 8/898; A61K 8/891; A61Q 5/02; A61Q 5/12

See application file for complete search history.

(56) References Cited

U.S. PATENT DOCUMENTS

| | | | | |
|---|---|---|---|---|
| 3,472,840 | A | 10/1969 | Stone et al. | |
| 3,589,978 | A | 6/1971 | Kamal et al. | |
| 3,869,454 | A | 3/1975 | Lang et al. | |
| 3,955,918 | A | 5/1976 | Lang | |
| 4,025,301 | A | 5/1977 | Lang | |
| 4,031,307 | A | 6/1977 | DeMartino et al. | |
| 4,131,576 | A | 12/1978 | Iovine et al. | |
| 4,137,180 | A | 1/1979 | Naik et al. | |
| 4,874,554 | A | 10/1989 | Lange et al. | |
| 5,708,151 | A | 1/1998 | Möckli | |
| 6,554,872 | B2 | 4/2003 | Genet et al. | |
| 6,881,230 | B2 | 4/2005 | Vidal | |
| 6,884,265 | B2 | 4/2005 | Vidal et al. | |
| 6,884,266 | B2 | 4/2005 | Vidal et al. | |
| 6,893,471 | B2 | 5/2005 | Vidal | |
| 7,001,436 | B2 | 2/2006 | Vidal et al. | |
| 7,022,143 | B2 | 4/2006 | Vidal et al. | |
| 7,060,110 | B2 | 6/2006 | Vidal et al. | |
| 7,261,743 | B2 | 8/2007 | Plos et al. | |
| 7,307,050 | B2 | 12/2007 | Terada | |
| 7,311,736 | B2 | 12/2007 | Burgaud et al. | |
| 7,407,516 | B2 | 8/2008 | Vidal | |
| 7,582,122 | B2 | 9/2009 | Daubresse et al. | |
| 7,870,633 | B2 | 1/2011 | Thiebaut | |
| 11,590,062 | B2 * | 2/2023 | Roy | A61K 8/463 |
| 11,938,205 | B2 * | 3/2024 | Roy | A61K 8/898 |
| 2006/0156488 | A1 | 7/2006 | David et al. | |
| 2006/0156489 | A1 | 7/2006 | David et al. | |
| 2006/0156490 | A1 | 7/2006 | David et al. | |
| 2006/0174422 | A1 | 8/2006 | David et al. | |
| 2008/0168607 | A1 | 7/2008 | David et al. | |
| 2016/0156479 | A1 | 6/2016 | Baek et al. | |

(Continued)

FOREIGN PATENT DOCUMENTS

| | | | |
|---|---|---|---|
| EP | 0714954 | A2 | 6/1996 |
| EP | 1006153 | A1 | 6/2000 |
| EP | 1377261 | A1 | 1/2004 |

(Continued)

OTHER PUBLICATIONS

International Search Report for counterpart Application No. PCT/EP2020/086563, dated Apr. 26, 2021.

Davies, J.T., "A Quantitative Kenetic Theory of Emulsion Type. I. Physical Chemistry of the Emulsifying Agent," Reprinted from: Gas/Liquid and Liquid/Liquid Interfaces, Proceedings of 2nd International Congress Surfact Activity, Butterworths, London, 1957, pp. 426-438.

Godfrey, K.M., "Cationic Emulsifiers in Cosmetics," J. Soc. Cosmetic Chemists, 17, (1966), pp. 17-27.

Griffin, William C., "Calculation of HLB Values of Non-Ionic Surfactants," J. Soc. Cosmet. Chemists, vol. 5 (1954), pp. 249-256.

(Continued)

*Primary Examiner* — Sean M Basquill
*Assistant Examiner* — Rajan Pragani
(74) *Attorney, Agent, or Firm* — The Marbury Law Group, PLLC

(57) ABSTRACT

The invention relates to a cosmetic composition comprising one or more polymers comprising one or more cationic or quaternized acrylamide and/or methacrylamide unit(s); a particular oil-in-water-type silicone emulsion; one or more surfactants; and optionally one or more direct dye(s)/pigment(s). The invention also relates a cosmetic process for washing and/or condition keratin fibres using said cosmetic composition.

16 Claims, No Drawings

(56) References Cited

U.S. PATENT DOCUMENTS

2017/0273881 A1* 9/2017 Facheris .................. A61K 8/36

FOREIGN PATENT DOCUMENTS

| | | | | |
|---|---|---|---|---|
| EP | 1377262 | A1 | 1/2004 | |
| EP | 1377263 | A2 | 1/2004 | |
| EP | 1377264 | A1 | 1/2004 | |
| EP | 1378544 | A2 | 1/2004 | |
| EP | 1399116 | A1 | 3/2004 | |
| EP | 1399117 | A1 | 3/2004 | |
| EP | 1399425 | A1 | 3/2004 | |
| EP | 1408919 | A2 | 4/2004 | |
| EP | 1416909 | A2 | 5/2004 | |
| EP | 1433471 | A1 | 6/2004 | |
| EP | 1433472 | A1 | 6/2004 | |
| EP | 1433473 | A1 | 6/2004 | |
| EP | 1433474 | A1 | 6/2004 | |
| EP | 1619220 | A1 | 1/2006 | |
| EP | 1619221 | A1 | 1/2006 | |
| EP | 1634926 | A1 | 3/2006 | |
| EP | 1637566 | A1 | 3/2006 | |
| EP | 1671560 | A1 | 6/2006 | |
| EP | 1671951 | A1 | 6/2006 | |
| EP | 1671952 | A1 | 6/2006 | |
| EP | 1671954 | A1 | 6/2006 | |
| EP | 1671955 | A1 | 6/2006 | |
| EP | 1671971 | A1 | 6/2006 | |
| EP | 1672033 | A2 | 6/2006 | |
| EP | 1674073 | A1 | 6/2006 | |
| EP | 1676567 | A1 | 7/2006 | |
| EP | 1679312 | A2 | 7/2006 | |
| EP | 1757660 | A1 | 2/2007 | |
| FR | 1492597 | A | 8/1967 | |
| FR | 2140205 | A1 | 1/1973 | |
| FR | 2189006 | A1 | 1/1974 | |
| FR | 2285851 | A1 | 4/1976 | |
| WO | 95/01772 | A1 | 1/1995 | |
| WO | 95/15144 | A1 | 6/1995 | |
| WO | 2006/063866 | A1 | 6/2006 | |
| WO | 2006/063867 | A2 | 6/2006 | |
| WO | 2006/063868 | A1 | 6/2006 | |
| WO | 2006/063869 | A2 | 6/2006 | |
| WO | 2012/072765 | A1 | 6/2012 | |
| WO | WO-2017108824 | A1 * | 6/2017 | ............... A61Q 5/02 |

OTHER PUBLICATIONS

Puisieux, F., et al., Galencia 5: Les systèmes disperses—Tome 1—Agents de surface et emulsions—Chapitre IV—Notions de HLB et du HLB critique,pp. 153-194—paragraph 1.1.2 Determination de HLB par voie experimental [Experimental determination of HLB], pp. 164-180.

* cited by examiner

COSMETIC COMPOSITION COMPRISING A POLYMER COMPRISING AT LEAST ONE CATIONIC (METH)ACRYLAMIDE UNIT, A PARTICULAR SILICONE AND AT LEAST ONE SURFACTANT

CROSS REFERENCE TO RELATED APPLICATIONS

This is a national stage application of PCT/EP2020/086563, filed internationally on Dec. 16, 2020, which claims priority to Indian Application No. 201921053705, filed on Dec. 24, 2019, the contents of both of which are incorporated by reference herein in their entireties.

The present invention relates to a cosmetic composition for treating keratin fibres, and in particular human keratin fibres such as hair, which comprises one or more polymers comprising at least one cationic or quaternized (meth)acrylamide unit, a specific oil-in-water-type silicone emulsion, and one or more surfactants.

The invention also relates to a cosmetic process for washing and/or conditioning keratin fibres using this composition.

Finally, the invention relates to the use of such a composition for washing and/or conditioning keratin fibres.

It is common practice to use detergent cosmetic compositions such as shampoos and shower gels, based essentially on surfactants, for washing keratin materials especially such as the hair and the skin. These compositions are applied to the keratin materials, which are preferably wet, and the lather generated by massaging or rubbing with the hands or a toiletry flannel makes it possible, after rinsing with water, to remove the diverse types of soiling initially present on the hair or the skin.

These compositions contain substantial contents of "detergent" surfactants, which, in order to be able to formulate cosmetic compositions with good washing power, must especially give them good foaming power.

The surfactants that are useful for this purpose are generally of anionic, nonionic and/or amphoteric type, and particularly of anionic type.

These compositions have generally a good washing power, but the intrinsic cosmetic properties associated with them nevertheless remain fairly poor, owing in particular to the fact that the relatively aggressive nature of such a cleaning treatment can, in the long run, lead to more or less pronounced damage to the hair fibre, this damage being associated in particular with the gradual removal of the lipids or proteins contained in or on the surface of this fibre.

Thus, in order to improve the cosmetic properties of the above detergent compositions, and more particularly those which are to be applied to sensitized hair (i.e. hair which has been damaged or made brittle, in particular under the chemical action of atmospheric agents and/or hair treatments such as permanent-waving, dyeing or bleaching), it is now common to introduce additional cosmetic agents known as conditioners into these compositions. These conditioners are intended mainly to repair or limit the harmful or undesirable effects induced by the various treatments or aggressions to which the hair fibres are subjected more or less repeatedly. They may, of course, also improve the cosmetic behaviour of natural hair.

The conditioners most commonly used to date in shampoos include cationic polymers, silicones and/or silicone derivatives, which give washed, dry or wet hair an ease-of disentangling, softness and smoothness which are markedly better than that which can be obtained with corresponding cleaning compositions from which they are absent.

In particular, it is known to use a mixture of silicone and cationic polymer. However, the compositions containing them still have numerous disadvantages, such as leading to an insufficient deposit of silicones on hair and impacting therefore strongly on their cosmetic properties.

Thus, there is a real need to provide cosmetic compositions, such as compositions for washing and/or conditioning keratin fibres, and in particular human keratin fibres, that allow overcoming the drawbacks described above, i.e. which effectively remove dirt and excess sebum and enhance cosmetic properties of said fibres, such as softness, smoothness, manageability and disentangling. These cosmetic properties may also be long-lasting.

The composition should give satisfactory silicone deposit on the keratin fibres.

The Applicant has now discovered that a cosmetic composition comprising one or more polymers comprising at least one cationic or quaternized (meth)acrylamide unit, a specific oil-in-water-type silicone emulsion, and one or more surfactants makes it possible to achieve the objectives outlined above.

Thus, the subject of the invention is especially a cosmetic composition comprising:

a. one or more polymers comprising one or more cationic or quaternized acrylamide and/or methacrylamide unit(s);
b. an oil-in-water emulsion having D50 particle size of less than 350 nm and comprising:
   - a silicone mixture comprising (i) a trialkylsilyl terminated dialkylpolysiloxane having a viscosity of from 40,000 to less than 100,000 mPa·s at 25° C. and (ii) an amino silicone having a viscosity of from 1,000 to 15,000 mPa·s at 25° C. and an amine value of from 2 to 10 mg of KOH per gram of amino silicone,
   - a mixture of emulsifiers comprising one or more nonionic emulsifiers, wherein the mixture of emulsifiers has a HLB value of from 10 to 16, and
   - water;
c. one or more surfactants.

This cosmetic composition, when applied on keratin fibres, in particular human keratin fibres such as hair, leads to an improvement of the condition and quality of hair, in terms of hair feel (e.g. smooth feel, soft feel, conditioned feel) and hair manageability (e.g., no or less frizz, styleability/shapeability, combing, detangling, desirable volume).

This cosmetic composition allows increasing the silicone deposition on hair when compared to a similar composition which does not contain the specific polymer a.

The composition according to the invention may optionally comprise one or more direct dye and/or pigment. In that option, the cosmetic composition allows increasing the silicone and dyes deposition on hair.

The present invention also relates to a cosmetic treatment process, in particular for washing and/or conditioning keratin fibres, preferably human keratin fibres such as the hair, using this composition.

Another subject-matter of the invention is the use of the composition according to the invention for washing and/or conditioning keratin fibres.

Other subject-matters, characteristics, aspects and advantages of the invention will emerge even more clearly on reading the description and the example that follows.

In the text herein below, unless otherwise indicated, the limits of a range of values are included in that range, for example in the expressions "between" and "ranging from . . . to . . . ".

Moreover, the expression "at least one" used in the present description is equivalent to the expression "one or more".

Polymer(s) Comprising at Least One Cationic or Quaternized (Meth)Acrylamide Unit The first essential component of the cosmetic composition according to the present invention is one or more polymer(s) comprising one or more cationic or quaternized (meth) acrylamide unit(s). These polymers are non-silicones, i.e. they do not contain any silicon (Si) atom.

Polymers comprising one or more cationic or quaternized (meth)acrylamide unit(s) can be cationic and/or amphoteric polymers.

By "cationic and/or amphoteric polymer(s)", it is understood one or more cationic polymers, one or more amphoteric polymers or the mixture of one or more cationic polymers, and of one or more amphoteric polymers.

The polymer(s) comprising one or more cationic or quaternized (meth)acrylamide units may be chosen from cationic polymers, amphoteric polymers and mixtures thereof. Most preferably, they are chosen from cationic polymers.

The cationic charge density of the polymers comprising one or more cationic or quaternized (meth)acrylamide units may preferably be lower than or equal to 6 meq/g, more preferentially lower than or equal to 5 meq/g, and better still lower than or equal to 4 meq/g. This cationic charge density advantageously ranges from 0.5 to 6 meq/g, better still from 1 to 5 meq/g, and even more preferably from 1.5 to 4 meq/g.

The term "cationic polymer" means any polymer comprising cationic groups and/or groups that can be ionized to cationic groups, and not comprising anionic groups and/or groups that can be ionized to anionic groups. Preferably, the cationic polymer is hydrophilic or amphiphilic. The preferred cationic polymers are chosen from those that contain units comprising primary, secondary, tertiary and/or quaternary amine groups that may either form part of the main polymer chain or may be borne by a side substituent directly connected thereto.

The polymers comprising one or more cationic or quaternized (meth)acrylamide units that can be used in the present invention are preferably chosen from homopolymers or copolymers comprising at least one of the units of the following formulae:

(II)

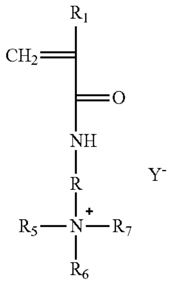

-continued (III)

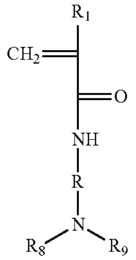

in which:

- $R_1$, which may be identical or different, denote a hydrogen atom or a $CH_3$ radical;
- R, which may be identical or different, denote a linear or branched $C_1$-$C_{12}$ alkyl radical, preferably a linear $C_1$-$C_6$ alkyl radical, optionally substituted by one or more hydroxyl radicals;
- $R_5$, $R_6$ and $R_7$, which may be identical or different, denote a linear or branched $C_1$-$C_{18}$ alkyl radical or a benzyl radical, preferably a linear or branched $C_1$-$C_6$ alkyl radical;
- $R_8$ and $R_9$, which may be identical or different, denote a hydrogen atom or a linear or branched $C_1$-$C_6$ alkyl radical, preferably methyl or ethyl; and
- $Y^-$ denotes an anion derived from a mineral or organic acid or a halide, preferably bromide, chloride, acetate, borate, citrate, tartrate, bisulfate, bisulfite, methosulfate, sulfate or phosphate anion.

More particularly the polymers comprising cationic or quaternized (meth)acrylamide units are chosen from copolymers comprising at least one unit of formula (II) as defined previously, and more preferably comprising at least one unit of formula (II) in which $R_1$ denotes a hydrogen atom, R represents a linear alkyl group having 3 carbon atoms and $R_5$, $R_6$ and $R_7$ represent a methyl.

The cationic polymers comprising one or more cationic or quaternized (meth)acrylamide unit(s) may also contain one or more units derived from comonomers that may be selected from the families of acrylamides, methacrylamides, diacetone acrylamides, acrylic or methacrylic acids or esters thereof, vinyllactams such as vinylpyrrolidone or vinylcaprolactam, and vinyl esters, preferably selected from the families of acrylamide and methacrylamides, and more preferentially acrylamide or methacrylamide.

Among these homo- or co-polymers, mention may be made of:

- homopolymers of Polyacrylamidopropyltrimonium halides, preferable Chloride, such as the product N-DURHANCE A-1000 from ASHLAND,
- copolymers of acrylamidopropyltrimonium chloride and acrylamide, such as the product sold under the name Salcare® SC 60 by the company BASF or sold under the name N-Hance SP 100 or N-Durhance AA2000 by the company Ashland,
- guar hydroxypropyltrimonium chlorure (and) acrylamidepropyl-trimonium chloride/acrylamide copolymer sold under the name of N-Hance 4572 (ex Aqualon aqua 4572 conditioning polymer) by the company Ashland,
- vinylpyrrolidone/methacrylamidopropyldimethylamine copolymers, such as those sold under the name STYLEZE CC 10 by ISP, quaternized vinylpyrrolidone/dimethylaminopropylmethacrylamide copolymers such as the product sold under the name GAFQUAT HS 100 by the company ISP, The polymers comprising one or more cationic or quaternized (meth)acrylamide units that can be used in the present invention can also be chosen from amphoteric polymers.

The term "amphoteric polymer" means any polymer comprising cationic groups and/or groups that can be ionized to cationic groups, and comprising anionic groups and/or groups that can be ionized to anionic groups Amphoteric polymers can be chosen more particularly from amphoteric polymers comprising a repetition of:

(i) one or more units derived from a monomer of (meth) acrylamide type, (ii) one or more units derived from a monomer of (meth) acrylamidoalkyltrialkylammonium type, and (iii) one or more units derived from an acidic monomer of (meth)acrylic acid type.

Preferably, the units derived from a monomer of (meth) acrylamide type (i) are units of structure (VI) below:

(VI)

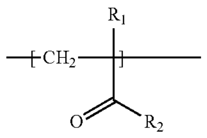

in which:

$R_1$ denotes a hydrogen atom or $CH_3$ radical; and $R_2$ denotes a $NR_3R_4$ radical, wherein $R_3$ and $R_4$, which may be identical or different, denote a hydrogen atom or a linear or branched $C_1$-$C_{12}$ alkyl radical, optionally substituted by one or more hydroxyl radicals, preferably $R_2$ denotes an amino, a dimethylamino, a tert-butylamino, a dodecylamino or a —NH—$CH_2OH$ radical.

Preferably, the said amphoteric polymer comprises a repetition of only one unit of formula (VI).

The unit derived from a monomer of (meth)acrylamide type of formula (VI) in which $R_1$ denotes a hydrogen atom and $R_2$ is an amino radical ($NH_2$) is particularly preferred. It corresponds to the acrylamide monomer per se.

Preferably, the units derived from a monomer of (meth) acrylamidoalkyltrialkylammonium type (ii) are units of structure (VII) below:

(VII)

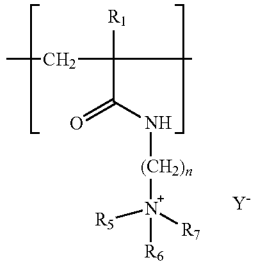

in which:

$R_3$ denotes a hydrogen atom or $CH_3$ radical;

$R_5$, $R_6$ and $R_7$, which may be identical or different, denote a linear or branched $C_1$-$C_6$ alkyl radical, preferably a linear or branched $C_1$-$C_4$ alkyl radical;

n denotes an integer ranging from 1 to 6, preferably from 1 to 4; and $Y^-$ denotes an anion derived from a mineral or organic acid or a halide, preferably bromide, chloride, acetate, borate, citrate, tartrate, bisulfate, bisulfite, methosulfate, sulfate or phosphate anion.

Preferably, the said amphoteric polymer comprises a repetition of only one unit of formula (VII).

Among these units derived from a monomer of (meth) acrylamidoalkyltrialkylammonium type of formula (VII), the ones that are preferred are those derived from the methacrylamidopropyltrimethylammonium chloride monomer, for which $R_1$ denotes a methyl radical, n is equal to 3, $R_5$, $R_6$ and $R_7$ denote a methyl radical, and $Y^-$ denotes a chloride anion.

Preferably, the units derived from a monomer of (meth) acrylic acid type (iii) are units of formula (VIII):

(VIII)

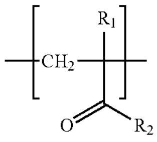

in which:

$R_1$ denotes hydrogen atom or $CH_3$ radical; and $R_2$ denotes a hydroxyl radical or a $NR_3R_4$ radical, wherein $R_3$ and $R_4$, which may be identical or different, denote a hydrogen atom or a linear or branched $C_1$-$C_{12}$ alkyl radical optionally substituted by a sulfonic group (—$SO_3H$), preferably $R_2$ denotes a —NH—$C(CH_3)_2$—$CH_2$—$SO_3H$ radical.

The preferred units of formula (VIII) correspond to the acrylic acid, methacrylic acid and 2-acrylamino-2-methylpropanesulfonic acid monomers.

Preferably, the unit derived from a monomer of (meth) acrylic acid type of formula (VIII) is that derived from acrylic acid, for which $R_1$ denotes a hydrogen atom and $R_2$ denotes a hydroxyl radical.

The acidic monomer(s) of (meth)acrylic acid type may be non-neutralized or partially or totally neutralized with an organic or mineral base.

Preferably, the said amphoteric polymer comprises a repetition of only one unit of formula (VIII).

According to a preferred embodiment of the invention, the amphoteric polymer(s) of this type comprise at least 30 mol % of units derived from a monomer of (meth)acrylamide type (i). Preferably, they comprise from 30 mol % to 70 mol % and more preferably from 40 mol % to 60 mol % of units derived from a monomer of (meth)acrylamide type.

The content of units derived from a monomer of (meth) acrylamidoalkyltrialkylammonium type (ii) may advantageously be from 10 mol % to 60 mol % and preferentially from 20 mol % to 55 mol %.

The content of units derived from an acidic monomer of (meth)acrylic acid type (iii) may advantageously be from 1 mol % to 20 mol % and preferentially from 5 mol % to 15 mol %.

According to a particularly preferred embodiment of the invention, the amphoteric polymer of this type comprises:

from 30 mol % to 70 mol % and more preferably from 40 mol % to 60 mol % of units derived from a monomer of (meth)acrylamide type (i), from 10 mol % to 60 mol % and preferentially from 20 mol % to 55 mol % of units derived from a monomer of (meth)acrylamidoalkyltrialkylammonium type (ii), and from 1 mol % to 20 mol % and preferentially from 5 mol % to 15 mol % of units derived from a monomer of (meth)acrylic acid type (iii).

Amphoteric polymers of this type may also comprise additional units, other than the units derived from a monomer of (meth)acrylamide type, of (meth)acrylamidoalkyltrialkylammonium type and of (meth)acrylic acid type as described above.

However, according to a preferred embodiment of the invention, the said amphoteric polymers consist solely of units derived from monomers (i) of (meth)acrylamide type, (ii) of (meth)acrylamidoalkyltrialkylammonium type and (iii) of (meth)acrylic acid type.

As examples of amphoteric polymers that are particularly preferred, mention may be made of acrylamide/methacrylamidopropyltrimethylammonium chloride/acrylic acid terpolymers. Such polymers are listed in the CTFA Dictionary (International Cosmetic Ingredient Dictionary) under the name Polyquaternium 53. Corresponding products are especially sold under the names Merquat 2003 and Merquat 2003 PR by the company Nalco.

Another preferred type of amphoteric polymers is the polymer comprising a repetition of:

(i) one or more non ionic units derived from a monomer of (meth)acrylate type, (ii) one or more units derived from a monomer of (meth) acrylamidoalkyltrialkylammonium type, and (iii) one or more units derived from an acidic monomer of (meth)acrylic acid type.

The monomer of (meth)acrylamidoalkyltrialkylammonium type and the acidic monomer of (meth)acrylic acid type (monomers (ii) and (iii) respectively) are as described above.

The non ionic monomers (i) of (meth)acrylate type are preferably chosen from $C_1$-$C_4$ alky acrylates and methacrylates. A preferred monomer is methyl acrylate.

As particularly preferred examples of such amphoteric polymers, mention may be made of acrylic acid/methylacrylamidopropyltrimdthylammonium chloride/methyl acrylates terpolymers. Such polymers are listed in the CTFA International Cosmetic Ingredient Dictionary under the name polyquaternium 47. Corresponding products are especially sold under the names Merquat 2001 and Merquat 2001N by the company Nalco.

The polymer(s) comprising one or more cationic or quaternized (meth)acrylamide units are preferably chosen from:

(meth)acrylamido($C_1$-$C_6$ alkyl)tri($C_1$-$C_4$ alkyl) ammonium halide/(meth)acrylamide copolymers, preferably (meth)acrylamidopropyltrimonium chloride/(meth) acrylamide copolymers, and more preferably acrylamidopropyltrimonium chloride/acrylamide copolymers, (meth)acrylamido($C_1$-$C_6$ alkyl)tri($C_1$-$C_4$ alkyl) ammonium halide/(meth)acrylamide/(meth)acrylic acid terpolymers, preferably (meth)acrylamidopropyltrimonium chloride/(meth)acrylamide/(meth)acrylic acid terpolymers, more preferably acrylamide/methacrylamidopropyltrimethylammonium chloride/acrylic acid terpolymers, (meth)acrylamido($C_1$-$C_6$ alkyl)tri($C_1$-$C_4$ alkyl) ammonium halide/($C_1$-$C_6$ alkyl) (meth)acrylate/(meth)acrylic acid terpolymers, preferably (meth)acrylamidopropyltrimonium chloride/($C_1$-$C_6$ alkyl) (meth)acrylate/(meth) acrylic acid terpolymers; more preferably acrylic acid/methylacrylamidopropyltrimethylammonium chloride/methyl acrylates terpolymers, and mixtures thereof.

More preferably, the polymer(s) comprising one or more cationic or quaternized (meth)acrylamide units are preferably chosen from:

(meth)acrylamido($C_1$-$C_6$ alkyl)tri($C_1$-$C_4$ alkyl) ammonium halide/(meth)acrylamide copolymers, preferably (meth)acrylamide-propyltrimonium chloride/(meth) acrylamide copolymers, and most preferably acrylamidopropyltrimonium chloride/acrylamide copolymers.

The total amount of polymer(s) comprising one or more cationic or quaternized (meth)acrylamide units present in the cosmetic composition of the present invention advantageously ranges from 0.01 to 5% by weight, preferably from 0.015 to 4% by weight, more preferentially from 0.02 to 2% by weight, better still from 0.04 to 1% by weight, and even more preferentially from 0.05 to 0.5% by weight, relative to the total weight of the cosmetic composition.

Silicone(s) in the Form of an Oil-In-Water Emulsion

The cosmetic composition according to the invention comprises an oil-in-water (or silicone-in-water) emulsion having D50 particle size of less than 350 nm and comprising:

a silicone mixture comprising (i) a trialkylsilyl terminated dialkylpolysiloxane having a viscosity of from 40,000 to less than 100,000 mPa·s at 25° C. and (ii) an amino silicone having a viscosity of from 1,000 to 15,000 mPa·s at 25° C. and an amine value of from 2 to 10 mg of KOH per gram of amino silicone;

a mixture of emulsifiers comprising one or more nonionic emulsifiers, wherein the mixture of emulsifiers has a HLB value of from 10 to 16; and water.

In the oil-in-water emulsion, or silicone-in-water emulsion, one liquid phase (the dispersed phase) is dispersed in the other liquid phase (the continuous phase); in the present invention, the silicone mixture, or silicone phase, is dispersed in the continuous aqueous phase.

The silicone mixture comprises one or more trialkylsilyl terminated dialkylpolysiloxanes, that are preferably of formula (IX):

$$R'_3SiO(R'_2SiO)_pSiR'_3$$

wherein:

R', same or different, is a monovalent hydrocarbon radical having from 1 to 18 carbon atoms, preferably from 1 to 6 carbon atoms, even better from 1 to 3 carbon atoms, more preferably methyl, and p is an integer of from 500 to 2,000, preferably of from 1,000 to 2,000.

The trialkylsilyl terminated (or end-blocked or $\alpha,\omega$-position) dialkylpolysiloxanes according to the invention have a viscosity of from 40,000 to less than 100,000 mPa·s (100,000 excluded) at 25° C., preferably a viscosity of from 40,000 to 70,000 mPa·s at 25° C., more preferably a viscosity of from 51,000 to 70,000 mPa·s at 25° C.

The trialkylsilyl terminated dialkylpolysiloxanes according to the invention are preferably linear but may contain additionally to the $R'_2SiO_{2/2}$ units (D-units) in formula (IX), $RSiO_{3/2}$ units (T-units) and/or $SiO_{4/2}$ units (Q-units), wherein R', same or different, is a monovalent hydrocarbon radical having from 1 to 18 carbon atoms.

Preferably, R', same or different, are alkyl radicals, preferably $C_1$-$C_{28}$ alkyl radicals, such as the methyl, ethyl, n-propyl, isopropyl, 1-n-butyl, 2-n-butyl, isobutyl, tert-butyl, n-pentyl, isopentyl, neopentyl and tert-pentyl radicals, hexyl radicals, such as the n-hexyl radical, heptyl radicals such as the n-heptyl radical, octyl radicals such as the n-octyl radical and isooctyl radicals, such as the 2,2,4-trimethylpentyl radical, nonyl radicals, such as the n-nonyl radicals, decyl radicals, such as the n-decyl radical, dodecyl radicals, such as the n-dodecyl radical, and octadecyl radicals, such as the n-octadecyl radical; alkenyl radicals such as the vinyl and ally radical; cycloalkyl radicals, such as the cyclopentyl, cyclohexyl, cycloheptyl and methylcyclohexyl radicals; aryl radicals, such as the phenyl, naphthyl, anthryl and phenanthryl radical; alkaryl radicals, such as the o-, m- and p-tolyl radicals, xylyl radicals and ethylphenyl radicals; and aralkyl radicals such as the benzyl radical and the a- and the b-phenylethyl radical. Most preferred is the methyl radical.

Preferably, the trialkylsilyl terminated dialkylpolysiloxanes are trimethylsilyl terminated PDMS (polydimethylsiloxanes or dimethicones).

The silicone mixture comprises one or more amino silicones, that are preferably of formula (X):

$$XR_2Si(OSiAR)_n(OSiR_2)_mOSiR_2X$$

wherein:

R, same or different, is a monovalent hydrocarbon radical having from 1 to 18 carbon atoms, preferably from 1 to 6 carbon atoms, even better from 1 to 3 carbon atoms, more preferably methyl;

X, same or different, is R or a hydroxyl (OH) or a $C_1$-$C_6$-alkoxy group; preferably X is R, i.e. a monovalent hydrocarbon radical having from 1 to 18 carbon atoms, preferably from 1 to 6 carbon atoms, even better from 1 to 3 carbon atoms, more preferably methyl;

A is an amino radical of the formula $—R^1—[NR^2—R^3—]_xNR^2_2$, or the protonated amino forms of said amino radical, wherein $R^1$ is a $C_1$-$C_6$-alkylene radical, preferably a radical of the formula $—CH_2CH_2CH_2—$ or $—CH_2CH(CH_3)CH_2—$, $R^2$, same or different, is a hydrogen atom or a $C_1$-$C_4$-alkyl radical, preferably a hydrogen atom, $R^3$ is a $C_1$-$C_6$-alkylene radical, preferably a radical of the formula $—CH_2CH_2—$, and x is 0 or 1;

and m+n is an integer from 50 to about 1000, preferably from 50 to 600.

Preferably, A is an amino radical of the formula $—R^1—[NR^2—R^3—]_xNR^2_2$, or the protonated amino forms of said amino radical, wherein $R^1$ is $—CH_2CH_2CH_2—$ or $—CH_2CH(CH_3)CH_2—$, $R^2$ are hydrogen atoms, $R^3$ is $—CH_2CH_2—$, and x is 1.

Preferably, R, same or different, are alkyl radicals, preferably $C_1$-$C_{28}$ alkyl radicals, such as the methyl, ethyl, n-propyl, isopropyl, 1-n-butyl, 2-n-butyl, isobutyl, tert-butyl, n-pentyl, isopentyl, neopentyl and tert-pentyl radicals, hexyl radicals, such as the n-hexyl radical, heptyl radicals such as the n-heptyl radical, octyl radicals such as the n-octyl radical and isooctyl radicals, such as the 2,2,4-trimethylpentyl radical, nonyl radicals, such as the n-nonyl radicals, decyl radicals, such as the n-decyl radical, dodecyl radicals, such as the n-dodecyl radical, and octadecyl radicals, such as the n-octadecyl radical; alkenyl radicals such as the vinyl and ally radical; cycloalkyl radicals, such as the cyclopentyl, cyclohexyl, cycloheptyl and methylcyclohexyl radicals; aryl radicals, such as the phenyl, naphthyl, anthryl and phenanthryl radical; alkaryl radicals, such as the o-, m- and p-tolyl radicals, xylyl radicals and ethylphenyl radicals; and aralkyl radicals such as the benzyl radical and the a- and the b-phenylethyl radical. Most preferred is the methyl radical.

The amino silicones according to the invention have a viscosity of from 1,000 to 15,000 mPa·s at 25° C., preferably of from 1,500 to 15,000 mPa·s.

The amino silicones according to the invention have an amine value of from 2 to 10 mg of KOH per gram of amino silicone, preferably of from 3.5 to 8 mg.

The mole percent of amine functionality is preferably in the range of from about 0.3 to about 8%.

Examples of amino silicones useful in the silicone mixture according to the invention include trialkylsilyl terminated amino silicone.

Most preferably, amino silicones are trimethylsilyl terminated aminoethylaminopropylmethylsiloxane, most preferably trimethylsilyl terminated aminoethylaminopropylmethylsiloxane-dimethylsiloxane copolymers. The amino radical A can be protonated partially or fully by adding acids to the amino silicone, wherein the salt forms of the amino radical are obtained. Examples of acids are carboxylic acids with 3 to 18 carbon atoms which can be linear or branched, such as formic acid, acetic acid, propionic acid, butyric acid, pivalic acid, sorbic acid, benzoic acid, salicylic acid. The acids are preferably used in amounts of from 0.1 to 2.0 mol per 1 mol of amino radical A in the amino silicone of formula (X).

The silicone mixture preferably comprises (i) one or more trialkylsilyl terminated dialkylpolysiloxanes having a viscosity of from 40,000 to less than 100,000 mPa·s at 25° C. in a quantity of from 70 to 90% by weight, preferably from 75 to 85% by weight and (ii) one or more amino silicones having a viscosity of from 1,000 to 15,000 mPa·s at 25° C. and an amine value of from 2 to 10 mg of KOH per gram of amino silicone, in a quantity of from 10 to 30% by weight, preferably from 15 to 25% by weight, relative to the total weight of the silicone mixture.

The oil-in-water emulsion further comprises a mixture of emulsifiers that comprises one or more nonionic emulsifiers. It could optionally comprise one or more cationic surfactants.

The mixture of emulsifiers has a HLB value from 10 to 16.

The nonionic emulsifiers can be chosen among the nonionic surfactants as described hereunder.

Mention may be made of alcohols, α-diols and $(C_{1-20})$ alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; or alternatively these compounds comprising at least one fatty chain comprising from 8 to 30 carbon atoms and especially from 16 to 30 carbon atoms.

Mention may also be made of condensates of ethylene oxide and of propylene oxide with fatty alcohols; polyethoxylated fatty amides preferably having from 2 to 30 ethylene oxide units, polyglycerolated fatty amides comprising on average from 1 to 5, and in particular from 1.5 to 4, glycerol groups; ethoxylated fatty acid esters of sorbitan preferably containing from 2 to 40 ethylene oxide units, fatty acid esters of sucrose, polyoxyalkylenated and preferably polyoxyethylenated fatty acid esters containing from 2 to 150 mol of ethylene oxide, including oxyethylenated plant oils, N—$(C_{6-24}$ alkyl)glucamine derivatives, amine oxides such as $(C_{10-14}$ alkyl)amine oxides or N—$(C_{10-14}$ acyl)aminopropylmorpholine oxides.

Mention may also be made of nonionic surfactants of alkyl(poly)glycoside type, represented especially by the following general formula:

$$R_1O—(R_2O)_t-(G)_v$$

in which:

$R_1$ represents a linear or branched alkyl or alkenyl radical comprising 6 to 24 carbon atoms and especially 8 to 18 carbon atoms, or an alkylphenyl radical whose linear or branched alkyl radical comprises 6 to 24 carbon atoms and especially 8 to 18 carbon atoms;

$R_2$ represents an alkylene radical comprising 2 to 4 carbon atoms,

G represents a sugar unit comprising 5 to 6 carbon atoms, t denotes a value ranging from 0 to 10 and preferably 0 to 4, v denotes a value ranging from 1 to 15 and preferably 1 to 4.

Preferably, the alkylpolyglycoside surfactants are compounds of the formula described above in which:

$R_1$ denotes a linear or branched, saturated or unsaturated alkyl radical comprising from 8 to 18 carbon atoms, $R_2$ represents an alkylene radical comprising 2 to 4 carbon atoms, t denotes a value ranging from 0 to 3 and preferably equal to 0, G denotes glucose, fructose or galactose, preferably glucose;

the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an alkyl(poly)glucoside surfactant. $C_8/C_{16}$ alkyl(poly)glycosides 1,4, and especially decyl glucosides and caprylyl/capryl glucosides, are most particularly preferred.

Among the commercial products, mention may be made of the products sold by the company COGNIS under the names PLANTAREN® (600 CS/U, 1200 and 2000) or PLANTACARE® (818, 1200 and 2000); the products sold by the company SEPPIC under the names ORAMIX CG 110 and ORAMIX NS 10; the products sold by the company BASF under the name LUTENSOL GD 70, or else the products sold by the company CHEM Y under the name AG10 LK.

The nonionic emulsifiers could preferably be chosen among ethoxylated aliphatic alcohols, polyoxyethylene surfactants, carboxylic esters, polyethylene glycol esters, sorbitol ester and their ethoxylated derivatives, glycol esters of fatty acids, carboxylic amides, monoalkanolamine condensates, polyoxyethylene fatty acid amides.

Preferably, nonionic emulsifiers are selected from:

(i) polyoxyalkylene alkyl ethers, especially (poly)ethoxylated fatty alcohols of formula:

$$R_3—(OCH_2CH_2)_cOH$$

with:

$R_3$ representing a linear or branched $C_8$-$C_{40}$ alkyl or alkenyl group, preferably $C_8$-$C_{30}$ alkyl or alkenyl group, optionally substituted with one or more hydroxyl groups, and c being an integer between 1 and 200 inclusive, preferentially between 2 and 150 and more particularly between 4 and 50, most preferably between 8 and 20.

The (poly)ethoxylated fatty alcohols are more particularly fatty alcohols comprising from 8 to 22 carbon atoms, oxyethylenated with 1 to 30 mol of ethylene oxide (1 to 30 OE);

(ii) polyoxyalkylene ($C_8$-$C_{32}$)alkylphenyl ethers, (iii) polyoxyalkylene sorbitan ($C_8$-$C_{32}$) fatty acid esters, especially polyethoxylated fatty acid esters of sorbitan preferably containing from 2 to 40 ethylene oxide units, most preferably from 2 to 20 ethylene oxide units; preferably polyoxyethylenated sorbitan ($C_{10}$-$C_{24}$) fatty acid esters preferably containing from 2 to 40 ethylene oxide units, most preferably from 2 to 20 ethylene oxide units; and (iv) polyoxyethylenated ($C_8$-$C_{32}$) fatty acid esters containing for example from 2 to 150 mol of ethylene oxide; preferably polyoxyethylenated ($C_{10}$-$C_{24}$) fatty acid esters containing for example from 2 to 150 mol of ethylene oxide.

Preferably, the nonionic emulsifiers could be selected from alkyl ether of polyalkyleneglycol and alkyl esters of polyalkyleneglycol; preferably of polyethyleneglycol (PEG).

Some useful emulsifiers are:

polyethyleneglycol octyl ether; polyethyleneglycol lauryl ether; polyethyleneglycol tridecyl ether; polyethyleneglycol cetyl ether; polyethyleneglycol stearyl ether; among these, mention may be made more particularly of trideceth-3, trideceth-10 and steareth-6.

polyethyleneglycol nonylphenyl ether; polyethyleneglycol dodecylphenyl ether; polyethyleneglycol cetylphenyl ether; polyethyleneglycol stearylphenyl ether;

polyethyleneglycol sorbitan monostearate, polyethyleneglycol sorbitan monooleate.

polyethyleneglycol stearate, and especially PEG-100 stearate.

Most preferably, the nonionic emulsifiers are chosen among steareth-6, PEG-100 stearate, trideceth-3 and trideceth-10 and their mixture; preferably, all these emulsifiers are present in the mixture of emulsifiers.

The mixture of emulsifiers could comprise one or more cationic emulsifiers that could be selected among tetraalkylammonium halides, tetraarylammonium halides, tetraalkylarylammonium halides, and their salts; quaternary ammonium compounds including salts; preferably, the cationic emulsifiers could be chosen among cetrimonium halides or behentrimonium halides, such as chloride.

The oil-in-water emulsion preferably comprises the mixture of emulsifiers in a total amount of from 5 to 15% by weight, preferably of from 8 to 15% by weight, most preferably of from 10 to 12% by weight, relative to the total weight of the emulsion.

The oil-in-water emulsion preferably comprises nonionic emulsifiers in a total amount of from 5 to 15% by weight, preferably of from 8 to 15% by weight, most preferably of from 10 to 12% by weight, relative to the total weight of the emulsion.

The oil-in-water emulsion preferably comprises cationic emulsifiers, when present, in a total amount of from 0.5 to 1.5% by weight, relative to the total weight of the emulsion.

The oil-in-water emulsion preferably comprises the silicone mixture in a total amount of from 40 to 60% by weight, preferably of from 45 to 55% by weight, relative to the total weight of the emulsion.

The oil-in-water emulsion preferably comprises the trialkylsilyl terminated dialkylpolysiloxane(s) in a total amount of from 35 to 45% by weight, preferably of from 38-42% by weight, relative to the total weight of the emulsion.

The oil-in-water emulsion preferably comprises the amino silicone(s) in a total amount of from 5 to 15% by weight, preferably of from 8-12% by weight, relative to the total weight of the emulsion.

The oil-in-water emulsion comprises water preferably in an amount of from 25 to 50% by weight, preferably of from 30 to 45% by weight, most preferably of from 35 to 42% by weight, relative to the total weight of the emulsion.

The oil-in-water emulsion could additionally comprise a biocide, such as phenoxyethanol, that could be present in the emulsion in a quantity of from 0.5 to 1% by weight, relative to the total weight of the emulsion.

A method of preparation of the oil-in-water emulsion preferably comprises:

- a step of mixing one or more trialkylsilyl terminated dialkylpolysiloxanes of viscosity of from 40,000 to less than 100,000 mPa·s at 25° C. and one or more amino silicones of viscosity of from 1,000 to 15,000 mPa·s at 25° C. and an amine value of from 2 to 10 mg of KOH per gram of amino silicone, at a temperature of from 15° C. to 40° C., preferably at 25° C., to obtain a mixed silicone fluid, then
- a step of adding a mixture of emulsifiers comprising one or more nonionic emulsifiers, wherein the mixture of emulsifiers has a HLB value from 10 to 16, to the mixed silicone fluid to obtain a silicone-emulsifier-mixture, then
- a step of homogenizing the silicone-emulsifier-mixture followed by
- a step of adding, preferably step-wise, water, preferably demineralized water, to obtain an oil-in-water emulsion having D50 particle size of less than 350 nm.

The method of preparation of the oil-in-water emulsion could further comprise an additional step of adding a biocide. Biocide could be added for preserving the emulsion against microbial contamination. The biocide could be added at the level of for preserving emulsion against microbial contamination and obtaining the said emulsion. The quantity of the biocide depends on the type of biocide and as recommended by the manufacturer.

The preparation of the mixture of emulsifiers could be made by mixing one or more nonionic emulsifiers.

The pH of the oil-in-water emulsion after neutralization (i.e. after addition of the biocide) is preferably of from 4 to 6.

The oil-in-water emulsion has D50 particle size of less than 350 nm, preferably of from 100 to 300 nm, more preferably from 150 to 250 nm, most preferably from 160 to 200 nm. It corresponds to the average hydrodynamic particle diameter. The D50 particle size is expressed in volume. The D50 particle size could be measured by using a device ZetaSizer from Malvern, UK, model Nano-ZS, which is based on the Photon Correlation Spectroscopy (PCS) method.

Particle Size Measurement

Emulsion particle size is measured by using a device ZetaSizer from Malvern, UK, model Nano-ZS which is based on the Photon Correlation Spectroscopy (PCS) method. The D50 value of particle size (average hydrodynamic particle diameter) is measured, wherein the evaluating algorithm is "cumulants analysis".

Take 0.5 g of the emulsion sample in a 250 ml beaker, 100 ml of demineralized water is poured into it and then mixed properly to get the sample test solution. The sample test solution is poured in the cuvette cell and is put into the slot of the instrument to measure the particle size of the emulsion. D50 is defined as the value of the particle diameter at 50% in the cumulative distribution. For example, if D50=170 nm, then 50% of the particles in the sample are larger than 170 nm, and 50% smaller than 170 nm or about 50% by volume of all droplets in said emulsion is 170 nm.

Viscosity Measurement

The viscosity, especially of the silicones or of the emulsion, is measured at 25° C.

For viscosities between 1000 to 40,000 mPa·s at 25° C.: the viscosity could be measured with an Anton Paar Rheometer; model MCR101, geometry single gap cylinder: CC27 spindle and shear rate of 1 $s^{-1}$ for 2 minutes, at 25° C.

For viscosities between 40,000 to 100,000 mPa·s at 25° C.: the viscosity could be measured with an Anton Paar Rheometer; model MCR101, 25-6 cone (Cone-plate geometry: 25 mm dia./6° cone); the "Zero gap" setting being made and with a shear rate of 1 $s^{-1}$ for 2 minutes, at 25° C.

Three measurements are made for each sample and the viscosity value is taken at 60 seconds. MCR Rheometer Series products work as per USP (US Pharmacopeia Convention) 912—Rotational Rheometer methods.

Amine Value Measurement

The amine value is determined by acid-base titration using a potentiometer [Make: Veego; Model: VPT-MG]. 0.6 g of sample is taken in a 500 ml beaker and a toluene-butanol 1:1 mixture is added and stirred to mix the sample thoroughly; then the sample solution is titrated with a 0.1(N) HCl solution. A determination of the blank value with the toluene-butanol 1:1 mixture is also done. The calculation of the amine value is done by the above mentioned potentiometer.

The amine value is calculated according to the formula:

$$56.11\times(V-V\ \mathrm{Blank})\times N/W\ \mathrm{mg\ KOH/g\ of\ sample},$$

where V=Volume of HCl required in ml, VBlank=Volume of HCl for blank value (without sample) with the toluene-butanol 1:1 mixture in ml; N=Normality of HCl, i.e. 0.1 N, W=weight of the sample taken in gram.

HLB Value

The term HLB is well known to those skilled in the art, and denotes the hydrophilic-lipophilic balance of a surfactant or emulsifier. In the present invention, HLB values refer to the values at 25° C.

The HLB can be measured by experimental determination or can be calculated.

Calculation of HLB value of nonionic surfactans is calculated according to the equation: HLB=(E+P)/5, with E being the weight percentage of oxyethylenecontent and P being the weight percentage of polyhydric alcohol content, described in to the publication Griffin, J. Soc. Cosm. Chem. 1954 (vol. 5, no 4), pp. 249-256.

It can also experimentally be determined according to the book of F. Puisieux and M. Seiller, entitled "Galenica 5: Les systèmes disperses—Tome I—Agents de surface et émulsions—Chapitre IV—Notions de HLB et de HLB critique, pp. 153-194—paragraph 1.1.2. Determination de HLB par voie experimentale [Experimental determination of HLB], pp. 164-180".

The calculated HLB is the preferred HLB values that should be taken into account.

Said calculated HLB could be defined as being the following:

"calculated HLB=20×molar mass of the hydrophilic part/total molar mass."

For an oxyethylenated fatty alcohol, the hydrophilic part corresponds to the oxyethylene units condensed onto the fatty alcohol and the "calculated HLB" then corresponds to the "Griffin HLB" as defined hereabove.

For an ester or an amide, the hydrophilic part is naturally defined as being beyond the carbonyl group, starting from the fatty chain(s).

For ionic surfactants/emulsifiers, the HLB value of individual surfactant/emulsifier can be calculated applying the Davies formula as described in Davies J T (1957), "A quantitative kinetic theory of emulsion type, I. Physical chemistry of the emulsifying agent", Gas/Liquid and Liquid/Liquid Interface (Proceedings of the International Congress of Surface Activity): 426-438.

According to the formula, the HLB is derived by summing the hydrophilic/hydrophobic contribution afforded by the structural components of the emulsifier: HLB=(hydrophilic groups numbers)−n(group number per $CH_2$ group)+7.

Approximate HLB values for some cationic emulsifiers are given in Table IV, in "Cationic emulsifiers in cosmetics", GODFREY, J. Soc. Cosmetic Chemists (1966) 17, pp 17-27.

When two emulsifiers A and B of known HLB are blended for use, the $HLB_{Mix}$ is said to be the required HLB for the mixture. This is expressed by the equation $(W_A HLB_A + W_B HLB_B)/(W_A + W_B) = HLB_{Mix}$, where $W_A$=the amount (weight) of the first emulsifier (A) used, and $W_B$=the amount (weight) of the second emulsifier (B); $HLB_A$, $HLB_B$=the assigned HLB values for emulsifiers A and B; $HLB_{Mix}$=the HLB of the mixture.

Said oil-in-water emulsion is for example described in WO 2017/108824.

The cosmetic composition according to the invention may comprise the oil-in-water emulsion b. in an amount ranging from 0.1% to 20% by weight, preferably from 0.3% to 15% by weight and better still from 0.5% to 12% by weight, better from 0.5 to 10%, even more preferentially from 0.5 to 8% by weight relative to the total weight of the composition.

The composition according to the invention comprises one or more surfactants that may be chosen from anionic, amphoteric or zwitterionic, non-ionic and cationic surfactants, and mixtures thereof.

In a preferred embodiment of the invention, the composition may comprise one or more anionic surfactants; preferably one or more anionic surfactants and one or more amphoteric surfactants. It may also comprise one or more non-ionic surfactants.

In another preferred embodiment of the invention, the composition may comprise one or more cationic surfactant. It may also comprise one or more non-ionic surfactants.

Anionic Surfactant(s)

The term "anionic surfactant" means a surfactant comprising, as ionic or ionizable groups, only anionic groups.

In the present description, a species is termed as being "anionic" when it bears at least one permanent negative charge or when it can be ionized as a negatively charged species, under the conditions of use of the composition of the invention (for example the medium or the pH) and not comprising any cationic charge.

The anionic surfactants may be sulfate, sulfonate and/or carboxylic (or carboxylate) surfactants. Needless to say, a mixture of these surfactants may be used.

It is understood in the present description that:

carboxylate anionic surfactants comprise at least one carboxylic or carboxylate function (—COOH or —$COO^-$) and may optionally also comprise one or more sulfate and/or sulfonate functions;

the sulfonate anionic surfactants comprise at least one sulfonate function (—$SO_3H$ or —$SO_3$—) and may optionally also comprise one or more sulfate functions, but do not comprise any carboxylate functions; and the sulfate anionic surfactants comprise at least one sulfate function but do not comprise any carboxylate or sulfonate functions.

The carboxylic anionic surfactants that may be used thus comprise at least one carboxylic or carboxylate function (—COOH or —$COO^-$).

They may be chosen from the following compounds: acylglycinates, acyllactylates, acylsarcosinates, acylglutamates; alkyl-D-galactosideuronic acids, alkyl ether carboxylic acids, alkyl($C_{6-30}$ aryl) ether carboxylic acids, alkylamido ether carboxylic acids; and also the salts of these compounds.

The alkyl and/or acyl groups of these compounds comprise from 6 to 30 carbon atoms, especially from 12 to 28, better still from 14 to 24 or even from 16 to 22 carbon atoms; the aryl group preferably denotes a phenyl or benzyl group.

These compounds are possibly polyoxyalkylenated, especially polyoxyethylenated, and then preferably comprising from 1 to 50 ethylene oxide units and better still from 2 to 10 ethylene oxide units.

Use may also be made of the $C_6$-$C_{24}$ alkyl monoesters of polyglycoside-polycarboxylic acids, such as $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates, and salts thereof.

Among the above carboxylic surfactants, mention may be made most particularly of polyoxyalkylenated alkyl(amido) ether carboxylic acids and salts thereof, in particular those comprising from 2 to 50 alkylene oxide and in particular ethylene oxide groups, such as the compounds sold by the company Kao under the name Akypo, The polyoxyalkylenated alkyl (amido) ether carboxylic acids that may be used are preferably chosen from those of formula (XI):

$$R_1 - (OC_2H_4)_n - OCH_2COOA \quad (XI)$$

wherein, $R_1$ represents a linear or branched $C_6$-$C_{24}$ alkyl or alkenyl radical, an alkyl($C_8$-$C_9$)phenyl radical, a radical $R_2CONH—CH_2—CH_2—$ with $R_2$ denoting a linear or branched $C_9$-$C_{21}$ alkyl or alkenyl radical, preferably, $R_1$ is a $C_8$-$C_{20}$ and preferably $C_8$-$C_{18}$ alkyl radical, and aryl preferably denotes phenyl, n is an integer or decimal number (average value) ranging from 2 to 24 and preferably from 2 to 10, A denotes H, ammonium, Na, K, Li, Mg or a monoethanolamine or triethanolamine residue.

It is also possible to use mixtures of compounds of formula (XI), in particular mixtures of compounds containing different groups $R_1$.

The polyoxyalkylenated alkyl(amido) ether carboxylic acids that are particularly preferred are those of formula (XI) in which:

$R_1$ denotes a $C_{12}$-$C_{14}$ alkyl, cocoyl, oleyl, nonylphenyl or octylphenyl radical, A denotes a hydrogen or sodium atom, and n varies from 2 to 20 and preferably from 2 to 10.

Even more preferentially, use is made of compounds of formula (XI) in which R denotes a $C_{12}$ alkyl radical, A denotes a hydrogen or sodium atom and n ranges from 2 to 10.

Preferentially, the carboxylic anionic surfactants are chosen, alone or as a mixture, from:

acylglutamates, especially of $C_6$-$C_{24}$ or even $C_{12}$-$C_{20}$, such as stearoylglutamates, and in particular disodium stearoylglutamate;

acylsarcosinates, especially of $C_6$-$C_{24}$ or even $C_{12}$-$C_{20}$, such as palmitoylsarcosinates, and in particular sodium palmitoylsarcosinate;

acyllactylates, especially of $C_{12}$-$C_{28}$ or even $C_{14}$-$C_{24}$, such as behenoyllactylates, and in particular sodium behenoyllactylate;

$C_6$-$C_{24}$ and especially $C_{12}$-$C_{20}$ acylglycinates;

($C_6$-$C_{24}$)alkyl ether carboxylates and especially ($C_{12}$-$C_{20}$) alkyl ether carboxylates;

polyoxyalkylenated ($C_6$-$C_{24}$)alkyl(amido) ether carboxylic acids, in particular those comprising from 2 to 50 ethylene oxide groups;

in particular in the form of alkali metal or alkaline-earth metal, ammonium or amino alcohol salts.

The sulfonate anionic surfactants that may be used comprise at least one sulfonate function (—$SO_3H$ or —$SO_3^-$).

They may be chosen from the following compounds: alkylsulfonates, alkylamidesulfonates, alkylarylsulfonates, α-olefinsulfonates, paraffin sulfonates, alkylsulfosuccinates, alkyl ether sulfosuccinates, alkylamidesulfosuccinates, alkylsulfoacetates, N-acyltaurates, acylisethionates; alkylsulfolaurates; and also the salts of these compounds. The alkyl groups of these compounds comprise from 6 to 30 carbon atoms, especially from 12 to 28, better still from 14 to 24 or even from 16 to 22 carbon atoms; the aryl group preferably denotes a phenyl or benzyl group.

These compounds are possibly polyoxyalkylenated, especially polyoxyethylenated, and then preferably comprising from 1 to 50 ethylene oxide units and better still from 2 to 10 ethylene oxide units.

Preferentially, the sulfonate anionic surfactants are chosen, alone or as a mixture, from:

$C_6$-$C_{24}$ and especially $C_{12}$-$C_{20}$ alkylsulfosuccinates, especially laurylsulfosuccinates;

$C_6$-$C_{24}$ and especially $C_{12}$-$C_{20}$ alkyl ether sulfosuccinates;

($C_6$-$C_{24}$)acylisethionates and preferably ($C_{12}$-$C_{18}$)acylisethionates, in particular in the form of alkali metal or alkaline-earth metal, ammonium or amino alcohol salts.

The sulfate anionic surfactants that may be used comprise at least one sulfate function (—$OSO_3H$ or —$OSO_3^-$).

They may be chosen from the following compounds: alkyl sulfates, alkyl ether sulfates, alkylamido ether sulfates, alkylaryl polyether sulfates, monoglyceride sulfates; and also the salts of these compounds.

The alkyl groups of these compounds comprise from 6 to 30 carbon atoms, especially from 12 to 28, better still from 14 to 24 or even from 16 to 22 carbon atoms; the aryl group preferably denotes a phenyl or benzyl group.

These compounds are possibly polyoxyalkylenated, especially polyoxyethylenated, and then preferably comprising from 1 to 50 ethylene oxide units and better still from 2 to 10 ethylene oxide units.

Preferentially, the sulfate anionic surfactants are chosen, alone or as a mixture, from:

alkyl sulfates, especially of $C_6$-$C_{24}$ or even $C_{12}$-$C_{20}$, alkyl ether sulfates, especially of $C_6$-$C_{24}$ or even $C_{12}$-$C_{20}$, preferably comprising from 2 to 20 ethylene oxide units;

in particular in the form of alkali metal or alkaline-earth metal, ammonium or amino alcohol salts.

When the anionic surfactant is in salt form, the said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Preferentially, the anionic surfactants are chosen, alone or as a mixture, from:

$C_6$-$C_{24}$ and especially $C_{12}$-$C_{20}$ alkyl sulfates;

$C_6$-$C_{24}$ and especially $C_{12}$-$C_{20}$ alkyl ether sulfates; preferably comprising from 2 to 20 ethylene oxide units;

$C_6$-$C_{24}$ and especially $C_{12}$-$C_{20}$ alkylsulfosuccinates, especially laurylsulfosuccinates;

$C_6$-$C_{24}$ and especially $C_{12}$-$C_{20}$ alkyl ether sulfosuccinates;

($C_6$-$C_{24}$)acylisethionates and preferably ($C_{12}$-$C_{18}$)acylisethionates;

$C_6$-$C_{24}$ and especially $C_{12}$-$C_{20}$ acylsarcosinates; especially palmitoylsarcosinates;

($C_6$-$C_{24}$)alkyl ether carboxylates, preferably ($C_{12}$-$C_{20}$) alkyl ether carboxylates;

polyoxyalkylenated ($C_6$-$C_{24}$)alkyl(amido) ether carboxylic acids and salts thereof, in particular those comprising from 2 to 50 alkylene oxide and in particular ethylene oxide groups;

$C_6$-$C_{24}$ and especially $C_{12}$-$C_{20}$ acylglutamates;

$C_6$-$C_{24}$ and especially $C_{12}$-$C_{20}$ acylglycinates;

in particular in the form of alkali metal or alkaline-earth metal, ammonium or amino alcohol salts.

Preferably, the anionic surfactants are of alkyl ether sulphate type and are preferably chosen from salts, in particular salts of alkali metals such as sodium salts, ammoniums salts, amine salts, amino alcohol salts or the salts of alkaline earth metals for example magnesium salts, of alkyl sulphates, of alkylamide sulphates, of alkyl ether sulphates, of alkylamido ether sulphates, of alkylaryl ether sulphates, of monoglyceride sulphates and mixtures thereof.

The alkyl radical of all these various compounds preferably contains from 8 to 24 carbon atoms, and the aryl radical preferably denoting a phenyl or benzyl group.

More preferentially, the anionic surfactant(s) is(are) selected from the anionic surfactants of alkyl ether sulphate type, and better still from $C_{12}$-$C_{14}$ alkyl ether sulphate salts, such as lauryl ether sulphate salts.

The anionic surfactants suitable in the composition of the present invention can be oxyethylenated and then preferably comprise from 1 to 50 ethylene oxide units.

The cosmetic composition according to the invention may comprise the one or more anionic surfactants in a total amount ranging from 0.1% to 40% by weight, preferably from 0.5% to 30%, better from 1% to 25% by weight and better still from 5% to 20% by weight, better from 10 to 15% by weight relative to the total weight of the composition.

Amphoteric or Zwitterionic Surfactant(s)

The composition according to the present invention may comprise one or more amphoteric or zwitterionic surfactant (s).

The amphoteric or zwitterionic surfactant(s) that may be used in the present invention may especially be secondary or tertiary aliphatic amine derivatives, optionally quaternized, in which the aliphatic group is a linear or branched chain containing from 8 to 22 carbon atoms, the said amine derivatives containing at least one anionic group, for instance a carboxylate, sulfonate, sulphate, phosphate or phosphonate group. Mention may be made in particular of ($C_8$-$C_{20}$)alkylbetaines, sulfobetaines, ($C_8$-$C_{20}$alkyl)amido ($C_3$-$C_8$alkyl)betaines or ($C_8$-$C_{20}$alkyl)amido($C_6$-$C_8$alkyl) sulfobetaines.

Among the secondary or tertiary aliphatic amine derivatives, optionally quaternized, that may be used, as defined above, mention may also be made of the compounds of respective structures (XII) and (XIII) below:

$$R_a—C(O)—N(Z)CH_2(CH_2)_mN^+(R_b)(R_c)—CH_2C(O)O^-,M^+,X^- \quad (XII)$$

wherein, $R_a$ represents a $C_6$-$C_{30}$ alkyl or alkenyl group derived from an acid $R_a$COOH preferably present in hydrolysed coconut oil, or a heptyl, nonyl or undecyl group;

$R_b$ represents a beta-hydroxyethyl group;

$R_c$ represents a carboxymethyl group;

$M^+$ represents a cationic counterion derived from an alkali metal or alkaline-earth metal, such as sodium, an ammonium ion or an ion derived from an organic amine; and $X^-$ represents an organic or mineral anionic counterion, preferably chosen from halides, acetates, phosphates, nitrates, ($C_1$-$C_4$)alkyl sulphates, ($C_1$-$C_4$)alkyl or ($C_1$-$C_4$) alkylaryl sulfonates, in particular methyl sulphate and ethyl sulphate;

m is equal to 0, 1 or 2; and

Z represents a hydrogen atom or a hydroxyethyl or carboxymethyl group.

Or alternatively $M^+$ and $X^-$ are absent;

$$R_{a'}—C(O)—N(Z)—CH_2—(CH_2)_{m'}—N(B)(B') \quad (XIII)$$

wherein

B represents the group $—CH_2—CH_2—O—X'$;

B' represents the group $—(CH_2)_zY'$, with z=1 or 2;

X' represents the group $—CH_2—C(O)OH$, $—CH_2—C(O)OZ'$, $—CH_2—CH_2—C(O)OH$, $—CH_2—CH_2—C(O)OZ'$, or a hydrogen atom;

Y' represents the group $—C(O)OH$, $—C(O)OZ'$, $—CH_2—CH(OH)—SO_3H$ or the group $—CH_2—CH(OH)—SO_3—Z'$;

Z' represents a cationic counterion derived from an alkali metal or alkaline-earth metal, such as sodium, an ammonium ion or an ion derived from an organic amine;

$R_{a'}$ represents a $C_6$-$C_{30}$ alkyl or $C_6$-$C_{30}$ alkenyl group of an acid $R_{a'}$—COOH, which is preferably present in coconut oil or in hydrolysed linseed oil, or an alkyl group, especially a $C_{17}$ alkyl group and its iso form, or an unsaturated $C_{17}$ group;

m' is equal to 0, 1 or 2; and

Z represents a hydrogen atom or a hydroxyethyl or carboxymethyl group.

The compounds of this type are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, cocoamphodipropionic acid and hydroxyethylcarboxymethylcocamidopropylamine.

Examples that may be mentioned include the cocoamphodiacetate sold by the company Rhodia under the trade name Miranol® C2M Concentrate or under the trade name Miranol Ultra C 32 and the product sold by the company Chimex under the trade name Chimexane HA.

Use may also be made of compounds of formula (XIV):

$$R_{a''}—NH—CH(Y'')—(CH_2)_n—C(O)NH(CH_2)_{n'}—N(R_d)(R_e) \quad (XIV)$$

wherein,

Y'' represents the group $—C(O)OH$, $—C(O)OZ''$, $—CH_2—CH(OH)—SO_3H$ or the group $CH_2—CH(OH)—SO_3—Z''$;

$R_d$ and $R_e$, independently of each other, represent a $C_1$-$C_4$ alkyl or hydroxyalkyl radical;

Z'' represents a cationic counterion derived from an alkali metal or alkaline-earth metal, such as sodium, an ammonium ion or an ion derived from an organic amine;

$R_{a''}$ represents a $C_6$-$C_{30}$ alkyl or alkenyl group of an acid $R_{a''}$—C(O)OH which is preferably present in coconut oil or in hydrolysed linseed oil; and n and n' denote, independently of each other, an integer ranging from 1 to 3.

Among the compounds of formula (XIV), mention may be made of the compound classified in the CTFA dictionary under the name sodium diethylaminopropyl cocoaspartamide and sold by the company Chimex under the name Chimexane HB.

Among the above-mentioned amphoteric or zwitterionic surfactants, it is preferred to use ($C_8$-$C_{20}$ alkyl)betaines such as cocoylbetaine (or cocobetaine), ($C_8$-$C_{20}$ alkyl)amido($C_2$-$C_8$ alkyl)betaines such as cocoylamidopropylbetaine, and mixtures thereof.

The cosmetic composition according to the invention may comprise the one or more amphoteric or zwitterionic surfactants in a total amount ranging from 0.01% to 25% by weight, preferably from 0.1 to 20% by weight, better from 0.5% to 15% by weight and better still from 1% to 10% by weight, better from 2 to 5% by weight relative to the total weight of the composition.

Cationic Surfactant(s)

The cationic surfactant(s) which can be used in the composition according to the invention comprise in particular optionally polyoxyalkylenated primary, secondary or tertiary fatty amines, and/or the salts or quaternary ammonium salts thereof, and mixtures thereof.

Mention may especially be made, as quaternary ammonium salts, for example, of:

those corresponding to the following general formula (XV):

(XV)

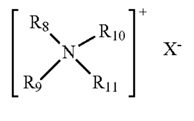

in which the groups $R_8$ to $R_{11}$, which may be identical or different, represent a linear or branched aliphatic group comprising from 1 to 30 carbon atoms, or an aromatic group such as aryl or alkylaryl, at least one of the groups $R_8$ to $R_{11}$ comprising from 8 to 30 carbon atoms and preferably from 12 to 24 carbon atoms; and $X^-$ is an anion chosen from the group of halides such as chloride, bromide and iodide, phosphates, acetates, lactates, ($C_1$-$C_4$)alkyl sulfates, and ($C_1$-$C_4$)alkyl- or ($C_1$-$C_4$)alkylarylsulfonates.

The aliphatic groups may comprise heteroatoms such as, especially, oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkylsufonates or ($C_1$-$C_4$)alkylarylsulfonates.

Preference is given, among the quaternary ammonium salts of formula (XV), on the one hand, to tetraalkylammonium chlorides, such as, for example, dialkyldimethylammonium or alkyltrimethylammonium chlorides, in which the alkyl group comprises approximately from 12 to 22 carbon atoms, in particular behenyltrimethylammonium, distearyldimethylammonium, cetyltrimethylammonium or benzyldimethylstearylammonium chlorides, or else palmitylamidopropyltrimethylammonium chloride or stearamidopropyldimethyl(myristyl acetate)ammonium chloride, sold under the name Ceraphyl® 70 by Van Dyk.

quaternary ammonium salts of imidazoline, such as, for example, those of the following formula (XVI):

(XVI)

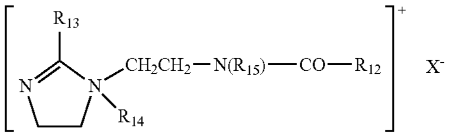

in which $R_{12}$ represents an alkenyl or alkyl group comprising from 8 to 30 carbon atoms, for example derived from tallow fatty acids, $R_{13}$ represents a hydrogen atom, a $C_1$-$C_4$ alkyl group or an alkenyl or alkyl group comprising from 8 to 30 carbon atoms, $R_{14}$ represents a $C_1$-$C_4$ alkyl group, $R_{15}$ represents a hydrogen atom or a $C_1$-$C_4$ alkyl group; $X^-$ is an anion chosen from the group of halides such as chloride, bromide and iodide, phosphates, acetates, lactates, ($C_1$-$C_4$)alkyl sulfates, and ($C_1$-$C_4$)alkyl- or ($C_1$-$C_4$)alkylarylsulfonates.

Preferably, $R_{12}$ and $R_{13}$ denote a mixture of alkenyl or alkyl groups comprising from 12 to 21 carbon atoms, for example derived from tallow fatty acids, $R_{14}$ denotes a methyl group and $R_{15}$ denotes a hydrogen atom. Such a product is sold, for example, under the name Rewoquat® W 75 by Rewo;

quaternary diammonium or triammonium salts, in particular of formula (XVII) below:

(XVII)

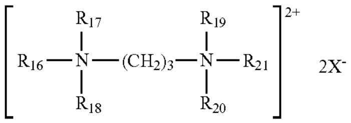

in which $R_{16}$ denotes an alkyl group comprising approximately from 16 to 30 carbon atoms, which is optionally hydroxylated and/or interrupted with one or more oxygen atoms, $R_{17}$ is chosen from hydrogen, an alkyl group comprising from 1 to 4 carbon atoms or a group $-(CH_2)_3-N^+(R_{16a})(R_{17a})(R_{18a})$, $R_{16a}$, $R_{17a}$, $R_{18a}$, $R_{18}$, $R_{19}$, $R_{20}$ and $R_{21}$, which may be identical or different, are chosen from hydrogen or an alkyl group comprising from 1 to 4 carbon atoms, and $X^-$ is an anion chosen from the group of halides, such as chloride, bromide and iodide, acetates, phosphates, nitrates, ($C_1$-$C_4$)alkyl sulfates, ($C_1$-$C_4$)alkyl- or ($C_1$-$C_4$)alkylarylsulfonates, in particular methyl sulfate and ethyl sulfate.

Such compounds are, for example, Finquat CT-P, sold by Finetex (Quaternium 89), and Finquat CT, sold by Finetex (Quaternium 75).

quaternary ammonium salts comprising one or more ester functions, for instance those of formula (XVIII) below:

(XVIII)

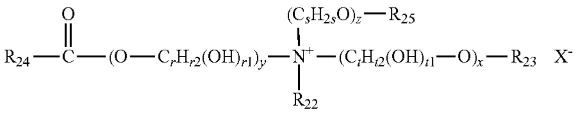

in which:

$R_{22}$ is chosen from $C_1$-$C_6$ alkyl groups and $C_1$-$C_6$ hydroxyalkyl or dihydroxyalkyl groups, $R_{23}$ is chosen from:

the group

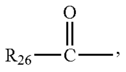

saturated or unsaturated, linear or branched $C_1$-$C_{22}$ hydrocarbon-based groups $R_{27}$, and a hydrogen atom, $R_{25}$ is chosen from:

the group

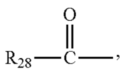

saturated or unsaturated, linear or branched $C_1$-$C_6$ hydrocarbon-based groups $R_{29}$, and a hydrogen atom, $R_{24}$, $R_{26}$ and $R_{28}$, which may be identical or different, are chosen from saturated or unsaturated, linear or branched $C_7$-$C_{21}$ hydrocarbon-based groups;

r, s and t, which may be identical or different, are integers having values from 2 to 6, r1 and t1, which may be identical or different, have the values 0 or 1, r2+r1=2 r and t1+t2=2 t, y is an integer ranging from 1 to 10, x and z, which may be identical or different, are integers having values from 0 to 10, $X^-$ is a simple or complex, organic or inorganic anion, with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group and more particularly a methyl or ethyl group.

Advantageously, the sum x+y+z has a value from 1 to 10.

When $R_{23}$ is a hydrocarbon-based group $R_{27}$, it can be long and have from 12 to 22 carbon atoms or be short and have from 1 to 3 carbon atoms.

When $R_{25}$ is a hydrocarbon-based group $R_{29}$, it preferably has from 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, have the value 0 or 1.

Advantageously, y is equal to 1.

Preferably, r, s and t, which may be identical or different, have the value 2 or 3 and more particularly still are equal to 2.

The anion $X^-$ is preferably a halide, preferably chloride, bromide or iodide, a ($C_1$-$C_4$)alkyl sulfate, or a ($C_1$-$C_4$)alkyl- or ($C_1$-$C_4$)alkylarylsulfonate. However, use may be made of methanesulfonate, phosphate, nitrate, tosylate, an anion derived from an organic acid, such as acetate or lactate, or any other anion which is compatible with the ammonium having an ester function.

The anion $X^-$ is more particularly still chloride, methyl sulfate or ethyl sulfate.

Use is more particularly made, in the composition according to the invention, of the ammonium salts of formula (XVIII) in which:

$R_{22}$ denotes a methyl or ethyl group, x and y are equal to 1, z is equal to 0 or 1, r, s and t are equal to 2, $R_{23}$ is chosen from:

the group

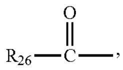, methyl, ethyl or $C_{14}$-$C_{22}$ hydrocarbon-based groups, and a hydrogen atom, $R_{25}$ is chosen from:

the group

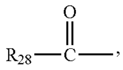, and a hydrogen atom, $R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Among the compounds of formula (XVIII), examples that may be mentioned include salts, especially the chloride or the methyl sulfate of diacyloxyethyldimethylammonium, diacyloxyethyl-hydroxyethylmethylammonium, monoacyloxyethyldihydroxyethylmethylammonium, triacyloxyethylmethylammonium or monoacyloxyethylhydroxyethyl-dimethylammonium, and mixtures thereof. The acyl groups preferably have from 14 to 18 carbon atoms and originate more particularly from a vegetable oil, such as palm oil or sunflower oil. When the compound comprises several acyl groups, the latter can be identical or different.

These products are obtained, for example, by direct esterification of triethanolamine, triisopropanolamine, alkyldiethanolamine or alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably a methyl or ethyl halide, a dialkyl sulfate, preferably a dimethyl or diethyl sulfate, methyl methanesulfonate, methyl para-toluenesulfonate, glycol chlorohydrin or glycerol chlorohydrin.

Such compounds are, for example, sold under the names Dehyquart® by Henkel, Stepanquat® by Stepan, Noxamium® by Ceca or Rewoquat® WE 18 by Rewo-Witco.

The composition according to the invention can comprise, for example, a mixture of quaternary ammonium mono-, di- and triester salts with a predominance by weight of diester salts.

Mention may be made, as examples of such compounds, of distearoylethylhydroxyethylmethylammonium or dipalmitoylethylhydroxyethylmethylammonium salts, and in particular the methosulfates.

Use may also be made of the ammonium salts containing at least one ester function that are described in U.S. Pat. Nos. 4,874,554 and 4,137,180.

Use may also be made of behenoylhydroxypropyl-trimethylammonium chloride, for example, sold by KAO under the name Quartamin BTC 131.

Preferably, the ammonium salts containing at least one ester function contain two ester functions.

Among the cationic surfactants, preference is more particularly given to those of formula (XV) such as cetyltrimethylammonium salts, behenyltrimethylammonium salts, and mixtures thereof, and more particularly behenyltrimethylammonium chloride, cetyltrimethylammonium chloride and mixtures thereof.

The cosmetic composition according to the invention may comprise the one or more cationic surfactants in a total amount ranging from 0.01% to 20% by weight, preferably from 0.1% to 15% by weight and better still from 0.5% to 10% by weight, better from 1 to 5% by weight relative to the total weight of the composition.

The total amount of surfactants may range from 0.1% to 40% by weight, preferably from 0.5% to 30% by weight and better still from 1% to 25% by weight, better from 5 to 20% by weight relative to the total weight of the composition.

The cosmetic composition of the invention may further comprise one or more direct dyes and/or pigments.

Direct Dye(s)

The cosmetic composition of the invention may further comprise one or more direct dyes.

The direct dye(s) may be chosen from synthetic direct dyes and natural direct dyes.

A direct dye is understood to be any dye which does not require the presence of a chemical oxidizing agent other than air for colouring.

A synthetic direct dye is understood to be any direct dye that does not exist in the natural state, including dyes obtained semi-synthetically.

Examples of suitable synthetic direct dyes that may be mentioned include azo, methine, carbonyl, azine, xanthene, nitro(hetero)aryl, tri(hetero)arylmethane, (metallo)porphyrin and phthalocyanine direct dyes, alone or as mixtures.

More particularly, the synthetic azo direct dyes include an —N═N— function in which the two nitrogen atoms are not simultaneously part of a ring. However, it is not excluded for one of the two nitrogen atoms of the sequence —N═N— to be part of a ring.

Examples of azo direct dyes that may be mentioned include the following dyes, described in Colour Index International, 3rd edition:

Disperse Red 17
Basic Red 22
Basic Red 76
Basic Yellow 57
Basic Brown 16
Basic Brown 17
Disperse Black 9.

The direct dyes of the methine family are more particularly compounds comprising at least one sequence chosen from >C═C< and —N═C< in which the two atoms are not simultaneously part of a ring. However, it is pointed out that one of the nitrogen or carbon atoms of the sequences may be part of a ring.

More particularly, the methine dyes are derived from methine, azomethine, hydrazono, mono- and diarylmethane, indoamine (or diphenylamine), indophenol, indoaniline and (hemi)cyanine compounds, such as styryl, streptocyanine, carbocyanine, azacarbocyanine, diazacarbocyanine and tetraazacarbocyanine, such as tetraazapentamethine, dyes, and the optical and geometric isomers thereof.

Among the azo, azomethine, methine or tetraazapentamethine direct dyes that may be used according to the invention, mention may be made of the cationic dyes described in patent applications WO 95/15144, WO 95/01772 and EP 714954; FR 2189006, FR 2285851, FR 2140205, EP 1378544, EP 1674073.

Among the indoamine dyes that may be used according to the invention, mention may be made of the following compounds:

2-β-hydroxyethlyamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N-(2'-chloro-4'-hydroxy)phenylacetylamino-6-methoxy-1,4-benzoquinone imine;
3-N-(3'-chloro-4'-methylamino)phenylureido-6-methyl-1,4-benzoquinone imine; and
3-[4'-N-(ethyl,carbamylmethyl)amino]phenylureido-6-methyl-1,4-benzoquinone imine.

Among the tetraazapentamethine dyes that may be used according to the invention, mention may be made of the following compounds appearing in the table below:

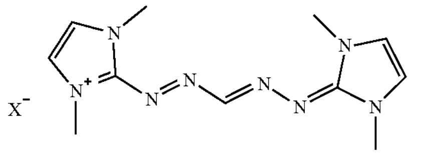

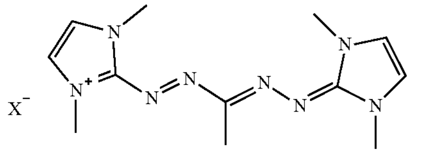

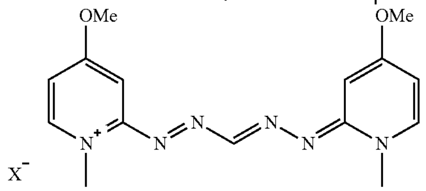

-continued

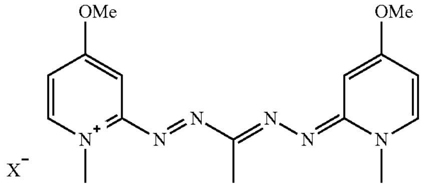

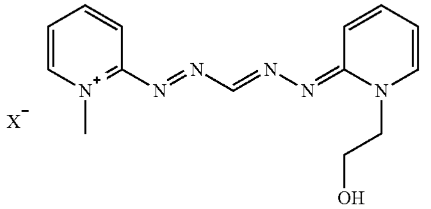

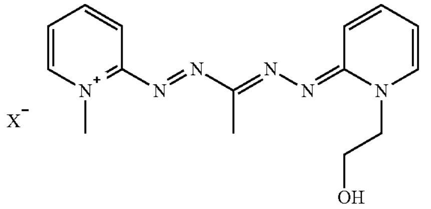

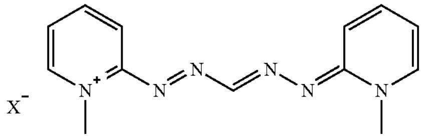

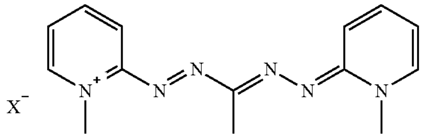

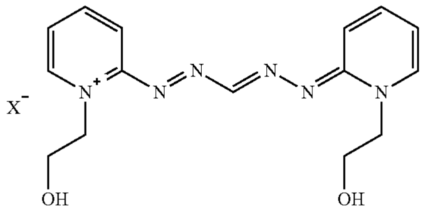

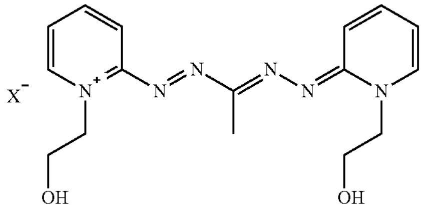

$X^-$ representing an anion preferably chosen from chloride, iodide, methyl sulfate, ethyl sulfate, acetate and perchlorate.

As regards the synthetic direct dyes of the carbonyl family, examples that may be mentioned include dyes chosen from quinone, acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes.

Among the quinone direct dyes, mention may be made of the following dyes:

Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99 and also the following compounds:

1-N-methylmorpholiniumpropylamino-4-hydroxyanthraquinone;
1-aminopropylamino-4-methylaminoanthraquinone;
1-aminopropylaminoanthraquinone;
5-β-hydroxyethyl-1,4-diaminoanthraquinone;
2-aminoethylaminoanthraquinone;
1,4-bis(β,γ-dihydroxypropylamino)anthraquinone.

As regards the synthetic direct dyes of the azine family, mention may be made in particular of azine, fluorindine, acridine, (di)oxazine and (di)thiazine dyes.

Examples of azine dyes that may be mentioned include the following compounds:

Basic Blue 17
Basic Red 2.

As regards the synthetic direct dyes of the xanthene family, mention may be made in particular of xanthene, thioxanthene and pyronine dyes.

The nitro(hetero)aryl synthetic direct dyes are more particularly nitrobenzene or nitropyridine direct dyes.

Among the nitrobenzene direct dyes that may be used according to the invention, mention may be made in a nonlimiting manner of the following compounds:

1,4-diamino-2-nitrobenzene;
1-amino-2 nitro-4-β-hydroxyethylaminobenzene;
1-amino-2 nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-β-hydroxyethylamino-2-nitro-4-(ethyl)(β-hydroxyethyl)aminobenzene;
1-amino-3-methyl-4-β-hydroxyethylamino-6-nitrobenzene;
1-amino-2-nitro-4-β-hydroxyethylamino-5-chlorobenzene;
1,2-diamino-4-nitrobenzene;
1-amino-2-β-hydroxyethylamino-5-nitrobenzene;
1,2-bis(β-hydroxyethylamino)-4-nitrobenzene;
1-amino-2-tris(hydroxymethyl)methylamino-5-nitrobenzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;
1-hydroxy-2-chloro-6-ethylamino-4-nitrobenzene;
1-hydroxy-2-chloro-6-amino-4-nitrobenzene;
1-hydroxy-6-bis(β-hydroxyethyl)amino-3-nitrobenzene;
1-β-hydroxyethylamino-2-nitrobenzene;
1-hydroxy-4-β-hydroxyethylamino-3-nitrobenzene.

Among the triarylmethane dyes that can be used according to the invention, mention may be made of the following compounds:

Basic Green 1
Basic Violet 3
Basic Violet 14
Basic Blue 7
Basic Blue 26.

As regards the (metallo)porphyrin or phthalocyanine synthetic direct dyes, use may be made of cationic or non-cationic compounds, optionally comprising one or more metals or metal ions, for instance alkali metals and alkaline-earth metals, zinc and silicon.

Examples of particularly suitable synthetic direct dyes that may be mentioned include nitrobenzene dyes; azo, methine, azomethine, hydrazono or styryl direct dyes; azacarbocyanines such as tetraazacarbocyanines (tetraazapentamethines); quinone direct dyes, and in particular anthraquinone, naphthoquinone or benzoquinone direct dyes; azine direct dyes; xanthene direct dyes; triarylmethane direct dyes; indoamine direct dyes, indigoid direct dyes, phthalocyanine direct dyes and porphyrin direct dyes, alone or as mixtures.

These dyes may be monochromophoric dyes (i.e. dyes comprising only one dye) or polychromophoric, preferably dichromophoric or trichromophoric, dyes; the chromophores may be identical or different, and from the same chemical family or otherwise. It should be noted that a polychromophoric dye comprises a plurality of groups each derived from a molecule that absorbs in the visible region between 400 and 800 nm. Furthermore, this absorbance of the dye does not require any prior oxidation thereof, or combination with one or more other chemical species.

In the case of polychromophoric dyes, the chromophores are connected together by means of at least one linker L, which may be cationic or non-cationic.

The linker L is preferably a linear, branched or cyclic $C_1$-$C_{20}$ alkyl chain which is optionally interrupted and/or terminated with at least i) a heteroatom (such as nitrogen N(R), $N^+R$, R', $Q^-$, oxygen or sulfur), ii) a group C(O), C(S), S(O) or $S(O)_2$ or iii) a combination thereof, optionally interrupted with at least one heterocycle which may or may not be fused to a phenyl nucleus, and which comprises at least one quaternized nitrogen atom forming part of said ring system, and optionally at least one other heteroatom (such as oxygen, nitrogen or sulfur), optionally interrupted with at least one substituted or unsubstituted phenyl or naphthyl group, optionally at least one quaternary ammonium group substituted with two $C_1$-$C_{15}$ alkyl groups which are optionally substituted; the linker does not contain a nitro, nitroso or peroxo group, and R and R', which may be identical or different, represent a hydrogen atom or a $C_1$-$C_6$ alkyl group which is optionally substituted, preferably with at least one hydroxyl group, and $Q^-$ represents an organic or mineral anionic counterion such as a halide or an alkyl sulfate.

If the heterocycles or aromatic nuclei are substituted, they are substituted, for example, with one or more $C_1$-$C_8$ alkyl groups optionally substituted with a hydroxyl, $C_1$-$C_2$ alkoxy, $C_2$-$C_4$ hydroxyalkoxy, acetylamino or amino group substituted with one or two $C_1$-$C_4$ alkyl groups, optionally bearing at least one hydroxyl group, or the two groups possibly forming, with the nitrogen atom to which they are attached, a 5- or 6-membered heterocycle, optionally comprising another nitrogen or non-nitrogen heteroatom; a halogen atom; a hydroxyl group; a $C_1$-$C_2$ alkoxy group; a $C_2$-$C_4$ hydroxyalkoxy group; an amino group; an amino group substituted with one or two identical or different $C_1$-$C_4$ alkyl groups, optionally bearing at least one hydroxyl group.

According to one particularly advantageous embodiment of the invention, the dye(s) are chosen from (poly)azo dyes such as (di)azo dyes; hydrazono dyes; (poly)methine dyes such as styryl dyes; anthraquinone dyes or naphthalimide dyes. Preferably, these dyes are (poly)cationic.

According to an even more preferred embodiment of the invention, the dyes are chosen from cationic dyes known as "basic dyes".

Mention may be made of the cationic hydrazono dyes of formulae (XIX) and (XIX'), the azo dyes (XX) and (XX') and the diazo dyes (XXI) below:

(XIX)

$Het^+$-C($R^a$)═N-N($R^b$)-Ar, $Q^-$ (XIX')

$Het^+$-N($R^a$)-N═C($R^b$)-Ar, $Q^-$ (XX)

$Het^+$-N═N-Ar, $Q^-$ (XX')

$Ar^+$-N═N-Ar'', $Q^-$ and (XXI)

$Het^+$-N═N-Ar'

-N═N-Ar, $Q^-$ in which formulae (XIX), (XIX'), (XX), (XX') and (XXI):

- $Het^+$ represents a cationic heteroaryl group, preferably bearing an endocyclic cationic charge, such as imidazolium, indolium or pyridinium, optionally substituted with one or more $C_1$-$C_8$ alkyl groups such as methyl;
- $Ar^+$ represents an aryl group, such as phenyl or naphthyl, bearing an exocyclic cationic charge, preferentially ammonium, particularly tri($C_1$-$C_8$ alkyl)ammonium such as trimethylammonium;
- Ar represents an aryl group, in particular phenyl, which is optionally substituted, preferentially with one or more electron-donating groups such as i) optionally substituted $C_1$-$C_8$ alkyl, ii) optionally substituted $C_1$-$C_8$ alkoxy, iii) (di)($C_1$-$C_8$ alkyl)amino optionally substituted on the alkyl group(s) with a hydroxyl group, iv) aryl($C_1$-$C_8$ alkyl)amino, or v) optionally substituted N—($C_1$-$C_8$ alkyl)-N-aryl($C_1$-$C_8$ alkyl)amino, or alternatively Ar represents a julolidine group;
- Ar' is an optionally substituted divalent (hetero)arylene group such as phenylene, particularly para-phenylene, or naphthalene, which are optionally substituted, preferably with one or more $C_1$-$C_8$ alkyl, hydroxyl or $C_1$-$C_8$ alkoxy groups;
- Ar'' is an optionally substituted (hetero)aryl group such as phenyl or pyrazolyl, which are optionally substituted, preferably with one or more $C_1$-$C_8$ alkyl, hydroxyl, (di)($C_1$-$C_8$ alkyl)amino, $C_1$-$C_8$ alkoxy or phenyl groups;
- $R^a$ and $R^b$, which may be identical or different, represent a hydrogen atom or a $C_1$-$C_8$ alkyl group, which is optionally substituted, preferentially with a hydroxyl group;
- or alternatively the substituent $R^a$ with a substituent of $Het^+$ and/or $R^b$ with a substituent of Ar form, together with the atoms that bear them, a (hetero)cycloalkyl;
- particularly, $R^a$ and $R^b$ represent a hydrogen atom or a $C_1$-$C_4$ alkyl group, which is optionally substituted with a hydroxyl group;
- $Q^+$ represents an organic or mineral anionic counterion, such as a halide or an alkyl sulfate.

In particular, the dyes of the invention are cationically charged, endocyclic, azo and hydrazono dyes of formulae (XIX), (XIX') and (XX) as defined previously. The dyes of formulae (XIX), (XIX') and (XX) described in patent applications WO 95/15144, WO 95/01772 and EP 714954 are more particularly preferred.

Dyes of the invention are preferably chosen from the following compounds:

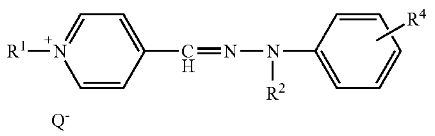

(XIX-1)

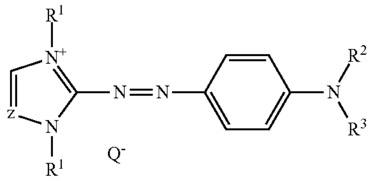

(XX-1)

in which formulae (XIX-1) and (XX-1):

- $R^1$ represents a $C_1$-$C_4$ alkyl group such as methyl;
- $R^2$ and $R^3$, which may be identical or different, represent a hydrogen atom or a $C_1$-$C_4$ alkyl group such as methyl; and
- $R^4$ represents a hydrogen atom or an electron-donating group such as optionally substituted $C_1$-$C_8$ alkyl, optionally substituted $C_1$-$C_8$ alkoxy, or (di)($C_1$-$C_8$ alkyl)amino optionally substituted on the alkyl group(s) with a hydroxyl group; particularly, $R^4$ is a hydrogen atom;
- Z represents a CH group or a nitrogen atom, preferentially CH;
- $Q^+$ is as defined previously.

In particular, the dyes of formulae (XIX-1) and (XX-1) are chosen from Basic Red 51, Basic Yellow 87 and Basic Orange 31 or their derivatives:

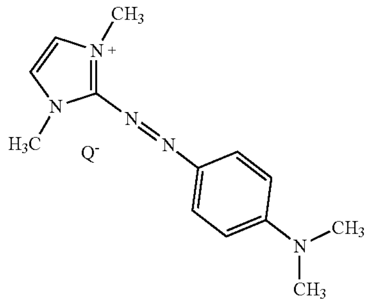

Basic Red 51

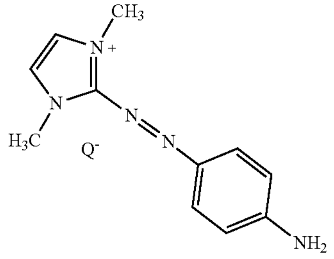

Basic Orange 31

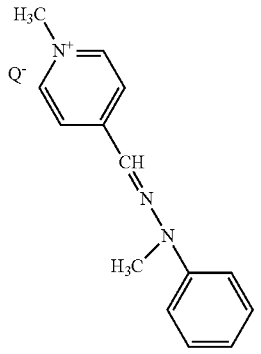

Basic Yellow 87 where $Q^-$ is as defined previously, and represents in particular a halide such as a chloride, or an alkyl sulfate such as methyl sulfate or mesityl.

Mention may also be made of 1-(4'-aminodiphenylazo)-2-methyl-4-bis(β-hydroxyethyl)aminobenzene.

Among the polychromophoric dyes, mention may be made more particularly of the symmetrical or non-symmetrical di- or trichromophoric azo and/or azomethine (hydrazone) dyes, comprising on the one hand at least one 5- or 6-membered aromatic heterocycle, optionally fused, which comprises at least one quaternized nitrogen atom forming part of said heterocycle, and optionally at least one other heteroatom (such as nitrogen, sulfur or oxygen), and, on the other hand, at least one optionally substituted phenyl or naphthyl group optionally bearing at least one group OR in which R represents a hydrogen atom, an optionally substituted $C_1$-$C_6$ alkyl group, an optionally substituted phenyl nucleus, or at least one group $N(R')_2$ with R', which may be identical or different, representing a hydrogen atom, an optionally substituted $C_1$-$C_6$ alkyl group or an optionally substituted phenyl nucleus; the groups R' possibly forming, with the nitrogen atom to which they are attached, a saturated 5- or 6-membered heterocycle, or else one and/or both of the groups R' may each form a saturated 5- or 6-membered heterocycle with the carbon atom of the aromatic ring that is ortho to the nitrogen atom.

Aromatic cationic heterocycles that may preferably be mentioned include 5- or 6-membered rings containing 1 to 3 nitrogen atoms and preferably 1 or 2 nitrogen atoms, one being quaternized; said heterocycle moreover being optionally fused to a benzene nucleus. It should similarly be noted that the heterocycle may optionally comprise another heteroatom other than nitrogen, for instance sulfur or oxygen.

If the heterocycles or phenyl or naphthyl groups are substituted, they are substituted, for example, with one or more $C_1$-$C_8$ alkyl groups optionally substituted with a hydroxyl, $C_1$-$C_2$ alkoxy, $C_2$-$C_4$ hydroxyalkoxy, acetylamino or amino group substituted with one or two $C_1$-$C_4$ alkyl groups, optionally bearing at least one hydroxyl group, or the two groups possibly forming, with the nitrogen atom to which they are attached, a 5- or 6-membered heterocycle, optionally comprising another nitrogen or non-nitrogen heteroatom; a halogen atom; a hydroxyl group; a $C_1$-$C_2$ alkoxy group; a $C_2$-$C_4$ hydroxyalkoxy group; an amino group; an amino group substituted with one or two identical or different $C_1$-$C_4$ alkyl groups, optionally bearing at least one hydroxyl group.

These polychromophores are connected together via at least one linker L as defined previously.

The bonding between the linker L and each chromophore generally takes place via a heteroatom substituent on the phenyl or naphthyl nucleus or via the quaternized nitrogen atom of the cationic heterocycle.

The dye may comprise identical or different chromophores.

As examples of such dyes, reference may be made in particular to patent applications EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063 866, WO 06/063 867, WO 06/063 868, WO 06/063 869, EP 1 408 919, EP 1 377 264, EP 1 377 262, EP 1 377 261, EP 1 377 263, EP 1 399 425, EP 1 399 117, EP 1 416 909, EP 1 399 116 and EP 1 671 560.

It is equally also possible to use cationic synthetic direct dyes which are mentioned in the following patent applications: EP 1 006 153, which describes dyes comprising two chromophores of anthraquinone type connected via a cationic linker; EP 1 433 472, EP 1 433 474, EP 1 433 471 and EP 1 433 473, which describe identical or different dichromophoric dyes, connected via a cationic or non-cationic linker, and also EP 06 291 333, which in particular describes dyes comprising three chromophores, one of them being an anthraquinone chromophore, to which are attached two chromophores of azo or diazacarbocyanine type or an isomer thereof.

The term "natural dyes" means any dye or dye precursor that is naturally occurring and that is produced either by extraction (and possibly purification) from a plant or animal matrix, optionally in the presence of natural compounds such as ash or ammonia, or by chemical synthesis.

Natural dyes that may be mentioned include lawsone, henna, curcumin, chlorophyllin, alizarin, kermesic acid, purpurin, purpurogallin, indigo, Tyrian purple, sorghum, carminic acid, catechin, epicatechin, juglone, bixin, betanin, quercetin, chromene dyes and chroman dyes, including haematein and brazilein, and laccaic acids.

Preferably, the natural dyes used in the invention are chosen from curcumin, chlorophyllin, chromene dyes, chroman dyes and laccaic acids.

According to the invention, the terms "chromene dye" and "chroman dye" mean dyes which comprise in their structure at least one bicycle of formula (XXII) below:

XXII

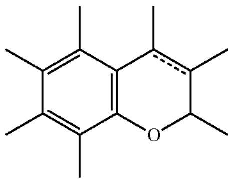

the endocyclic bond $\overset{----}{—}$ representing a carbon-carbon single bond or a carbon-carbon double bond, as illustrated by formula XXII-1 denoting the chromene family and formula XXII-2 denoting the chroman family below:

XXII-1

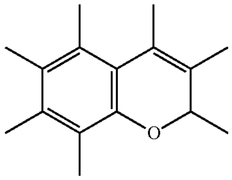

XXII-2

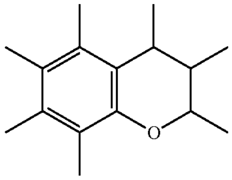

More particularly, the dyes having in their structure a bicycle of formula (XXII) are chosen from the dyes having the following formulae:

formula (XXIII), comprising in its structure the bicycle of formula XXII-2, (XXIII)

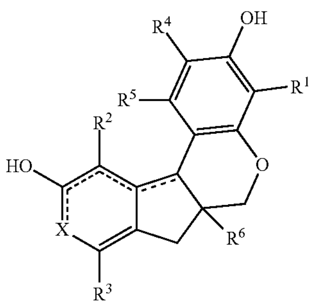

in which:

i) $\overset{----}{—}$ represents a carbon-carbon single bond or a carbon-carbon double bond, the sequence of these $\overset{----}{—}$ bonds denoting two carbon-carbon single bonds and two carbon-carbon double bonds, said bonds being conjugated, ii) X represents a group:

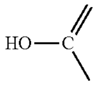

or

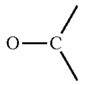

iii) $R^1$, $R^2$, $R^3$, $R^4$, $R^5$ and $R^6$, which may be identical or different, represent, independently of each other, a hydrogen atom, a hydroxyl group, an optionally substituted alkyl group, an optionally substituted alkoxy group or an optionally substituted acyloxy group, and also the tautomeric and/or mesomeric forms thereof, the stereoisomers thereof, the addition salts thereof with a cosmetically acceptable acid or base, and the hydrates thereof, and formula (XXIV), comprising in its structure the bicycle of formula XXII-1, (XXIV)

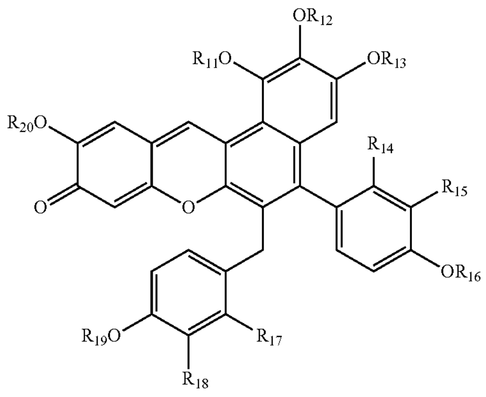

in which:

$R_{11}$, $R_{12}$, $R_{13}$, $R_{16}$, $R_{19}$ and $R_{20}$, which may be identical or different, represent, independently of each other, a hydrogen atom or a $C_1$-$C_4$ alkyl group, $R_{14}$, $R_{15}$, $R_{17}$ and $R_{18}$, which may be identical or different, represent, independently of each other, a hydrogen atom, a hydroxyl group or a $C_1$-$C_4$ alkoxy group, and also the tautomeric and/or mesomeric forms thereof, the stereoisomers thereof, the addition salts thereof with a cosmetically acceptable acid or base, and the hydrates thereof.

As regards the dyes of formula (XXIII) as defined previously, they may be in two tautomeric forms noted (XXIIIa) and (XXIIIb):

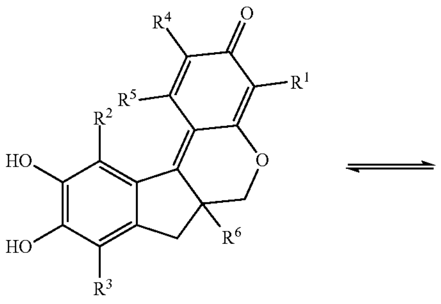

(XXIIIa)

-continued

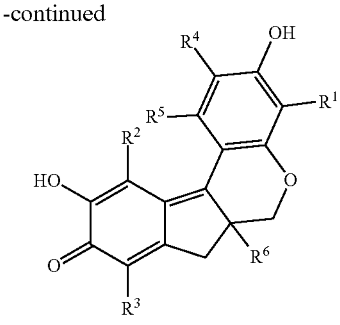

(XXIIIb)

The alkyl groups mentioned in the preceding definitions of the substituents are linear or branched, saturated, generally $C_1$-$C_{20}$, particularly $C_1$-$C_{10}$ and preferably $C_1$-$C_6$ hydrocarbon-based groups, such as methyl, ethyl, propyl, butyl, pentyl and hexyl.

The alkoxy groups are alkyl-oxy groups with alkyl groups as defined previously and preferably the alkoxy groups are $C_1$-$C_{10}$, such as methoxy, ethoxy, propoxy and butoxy.

The alkyl or alkoxy groups, when they are substituted, may be substituted with at least one substituent borne by at least one carbon atom, chosen from:
- a halogen atom;
- a hydroxyl group;
- a $C_1$-$C_2$ alkoxy group;
- a $C_1$-$C_{10}$ alkoxycarbonyl group;
- a $C_2$-$C_4$ (poly)hydroxyalkoxy group;
- an amino group;
- a 5- or 6-membered heterocycloalkyl group;
- an optionally cationic 5- or 6-membered heteroaryl group, preferentially imidazolium, optionally substituted with a ($C_1$-$C_4$)alkyl group, preferentially methyl;
- an amino group substituted with one or two identical or different $C_1$-$C_6$ alkyl groups, optionally bearing at least:
- one hydroxyl group;
- an amino group optionally substituted with one or two optionally substituted $C_1$-$C_3$ alkyl groups, it being possible for said alkyl groups to form, with the nitrogen atom to which they are attached, a saturated or unsaturated and optionally substituted 5- to 7-membered heterocycle, optionally comprising at least one other nitrogen or non-nitrogen heteroatom,
- a quaternary ammonium group —$N^+R'R''R'''$, $M^-$ for which R', R'' and R''', which may be identical or different, represent a hydrogen atom or a $C_1$-$C_4$ alkyl group; and $M^-$ represents the counterion of the corresponding organic or mineral acid or of the corresponding halide;
- or an optionally cationic 5- or 6-membered heteroaryl group, preferentially imidazolium, optionally substituted with a ($C_1$-$C_4$) alkyl group, preferentially methyl;
- an acylamino group (—NR—COR') in which the group R is a hydrogen atom or a $C_1$-$C_4$ alkyl group optionally bearing at least one hydroxyl group and the group R' is a $C_1$-$C_2$ alkyl group;
- a carbamoyl group ($(R)_2N$—CO—) in which the groups R, which may be identical or different, represent a hydrogen atom or a $C_1$-$C_4$ alkyl group optionally bearing at least one hydroxyl group;
- an alkylsulfonylamino group ($R'SO_2$—NR—) in which the group R represents a hydrogen atom or a $C_1$-$C_4$ alkyl group optionally bearing at least one hydroxyl group and the group R' represents a $C_1$-$C_4$ alkyl group, or a phenyl group;
- an aminosulfonyl group ($(R)_2N$—$SO_2$—) in which the groups R, which may be identical or different, represent a hydrogen atom or a $C_1$-$C_4$ alkyl group optionally bearing at least one hydroxyl group;
- a carboxylic group in acid or salified form (preferably with an alkali metal or a substituted or unsubstituted ammonium);
- a cyano group;
- a nitro group;
- a carboxyl or glycosylcarbonyl group;
- a phenylcarbonyloxy group optionally substituted with one or more hydroxyl groups;
- a glycosyloxy group; and
- a phenyl group optionally substituted with one or more hydroxyl groups.

The term "glycosyl group" means a group originating from a mono- or polysaccharide.

Preferably, the alkyl or alkoxy groups of formula (XXIII) are unsubstituted.

According to one particular embodiment of the invention, the dyes of formula (XXIII) comprise a group $R^6$ which represents a hydroxyl group.

In one preferred variant, X represents a group O═C.

Another particular embodiment of the invention relates to the dyes of formula (XXIII), for which the group $R^1$ represents a hydrogen atom or a hydroxyl group.

More particularly, the dyes of formula (XXIII) are chosen from haematein and brazilein.

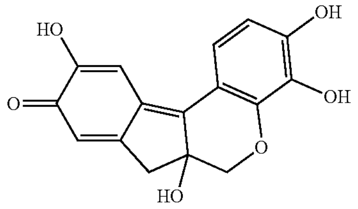

Haematein

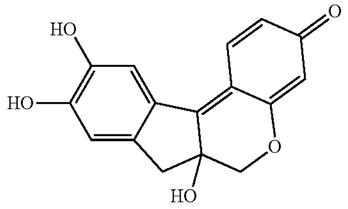

Brazilein

Brazilein is a conjugated form of a chroman compound of formula XXII-2. The tautomeric structures (XXIIIa) and (XXIIIb) illustrated above are found in the scheme below.

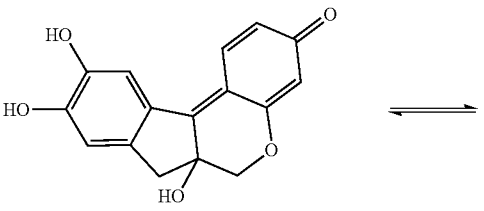

-continued

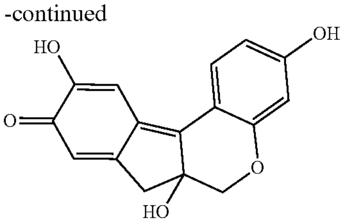

Brazilein and haematein or the haematoxylin/haematein and brazilin/brazilein pairings may be obtained synthetically or by extraction of plants known to be rich in these dyes.

The dyes of formula (XXIII) may be used in the form of extracts. Use may be made of the following plant extracts (genus and species): *Haematoxylon campechianum, Haematoxylon brasiletto, Caesalpinia echinata, Caesalpinia sappan, Caesalpinia spinosa* and *Caesalpinia brasiliensis.*

The extracts are obtained by extraction of various plant parts, such as, for example, the root, wood, bark or leaves.

According to a particular embodiment of the invention, the natural dyes of formula (XXIII) are obtained from logwood, pernambuco wood, sappan wood and Brazil wood.

The salts of the dyes of formulae (XXIII) and (XXIV) of the invention may be salts of cosmetically acceptable acids or bases.

The acids may be mineral or organic. Preferably, the acid is hydrochloric acid, which results in chlorides.

The bases may be mineral or organic. In particular, the bases are alkaline hydroxides, such as sodium hydroxide, resulting in sodium salts.

Preferably, the dye(s) of formulae (XXIII) and (XXIV) included in the composition according to the invention are derived from plant extracts. Use may also be made of mixtures of plant extracts.

The natural extracts of the dyes according to the invention may be in the form of powders or liquids. Preferably, the extracts are in powder form.

In another variant of the invention, the natural dyes are chosen from laccaic acids.

For the purposes of the present invention, the term "laccaic acid" means a compound having in its structure a unit of the type:

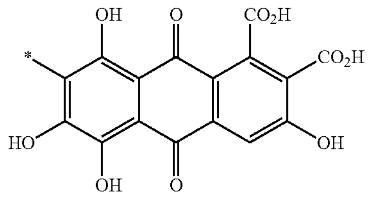 [SMILES: *c1c(O)c(O)c2c(c1O)C(=O)c1c(cc(O)c(C(=O)O)c1C(=O)O)C2=O]

Preferably, the laccaic acids of the invention are of formula (XXV) below:

(XXV)

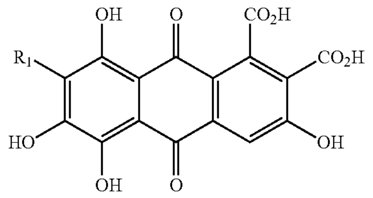

with $R_1$ denoting a phenyl group substituted with at least one hydroxyl group, and preferably with a hydroxyl group that is advantageously in the ortho position relative to the bond attaching it to the fused nuclei.

In particular, the phenyl group $R_1$ comprises, besides a hydroxyl group, at least one group $—CH_2R_2$, $R_2$ denoting an acetamidomethyl ($CH_3CONHCH_2—$), hydroxymethyl ($HOCH_2—$) or 2-aminoacetic acid ($HO_2C(NH_2)CH—$) group.

Preferentially, the laccaic acids of the invention are chosen from laccaic acids A, B, C and D, or mixtures thereof, and more particularly chosen from A, B and C, or mixtures thereof.

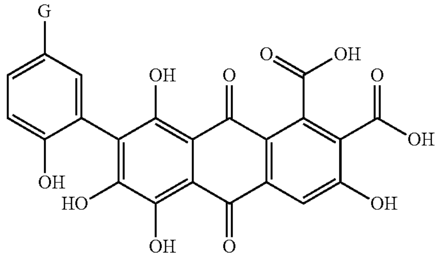

Laccaic acid A G: $—CH_2CH_2NHC(O)CH_3$
Laccaic acid B G: $—CH_2CH_2OH$
Laccaic acid C G: $—CH_2CH(NH_2)C(O)OH$
Laccaic acid D G: $—CH_2CH_2NH_2$ Laccaic acids A, B, C and D A laccaic acid according to the invention that may in particular be used is the dye CI Natural Red 25, CI 75450, CAS-60687-93-6, which is often referred to as laccaic acid. This is a dye of natural origin originating from the secretions of an insect, *Coccus laccae* (Lacifer Lacca Kerr), which is generally found on the twigs of certain trees native to South-East Asia.

CI Natural Red 25 generally contains two major constituents in its composition: laccaic acid A and laccaic acid B. It may also contain a small amount of laccaic acid C.

Needless to say, use may also be made of the purified forms of the laccaic acids of formula (XXV).

Even more preferentially, the natural direct dyes are chosen from haematein and brazilein.

Preferably, direct dyes are chosen from acidic (or anionic) direct dyes.

When it(they) is(are) present, the total amount of the direct dye(s) usually ranges from 0.001% to 10% by weight, and preferably from 0.01% to 5% by weight, still better from 0.05 to 4% by weight better 0.2 to 3%, more better 0.5-2% by weight relative to the total weight of the composition of the invention.

Pigment(s)

The cosmetic composition of the invention may further comprise one or more pigments.

For the purposes of the present invention, the term "pigment" means organic or mineral, white or coloured particles of any form, which are insoluble in the medium of the composition and which give the composition a colour.

The term "mineral" encompasses natural or synthetic chemical compounds that are inorganic. Mineral substances are mainly in a crystalline form.

Examples of mineral or inorganic pigments that may especially be mentioned include:

- white pigments such as titanium dioxide, zinc oxide, zirconium oxide and cerium oxide;
- coloured pigments such as red iron oxide, yellow iron oxide, black iron oxide, chromium oxide, chromium hydroxide, Prussian blue, ultramarine blue, chromium hydrate, ferric blue, inorganic blue pigments, carbon black, lower titanium oxides, manganese violet, cobalt violet, and metal powders such as aluminium powder and copper powder;
- nacreous pigments such as bismuth oxychloride, mica/titanium, essence of pearl, powder prepared by coating synthetic mica with titanium dioxide, powder prepared by coating silica flakes with titanium dioxide, which is available under the brand name Metashine from Nippon Sheet Glass Co., Ltd, powder prepared by coating alumina flakes with tin oxide and titanium dioxide, powder prepared by coating aluminium flakes with titanium dioxide, powder prepared by coating copper flakes with silica, sold by the company Eckert Inc. USA, powder prepared by coating bronze flakes with silica, and powder prepared by coating aluminium flakes with silica;

Examples of organic pigments are Colour Index (CI) yellow pigments, CI orange pigments and tar-based pigments prepared in lacquer form, and dyes existing in the natural state prepared in lacquer form.

The tar-based dyes include, for example, the dyes Red No. 3, Red No. 10, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207.

The natural dyes include powders such as carmine, laccaic acid, carsamine, brazilin and crocin.

When it(they) is(are) present, the total amount of the pigment(s) usually ranges from 0.01% to 15% by weight, preferably from 0.05 to 10% by weight, still better from 0.1 to 5% by weight, better from 0.2 to 4%; even more preferentially from 0.3 to 2% by weight, relative to the total weight of the composition of the invention.

Additional Cationic Polymer(s)

The cosmetic composition according to the present invention may further comprise one or more additional cationic polymers different from the polymers comprising one or more cationic or quaternized (meth)acrylamide units described above. These optional additional cationic polymers do not contain any cationic/quaternized acrylamide and/or methacrylamide unit and are non silicone polymers.

The additional cationic polymers that may be used preferably have a weight-average molar mass (Mw) of between 500 and $5\times10^6$ approximately and preferably between $10^3$ and $3\times10^6$ approximately.

Among the additional cationic polymers, mention may be made more particularly of:

(1) Cationic polysaccharides, especially cationic celluloses and galactomannan gums. Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are especially described in French patent 1 492 597, and mention may be made of the polymers sold under the name UCARE POLYMER "JR" (JR 400 LT, JR 125 and JR 30M) or "LR" (LR 400 or LR 30M) by the company Amerchol. These polymers are also defined in the CTFA dictionary as quaternary ammoniums of hydroxyethylcellulose that have reacted with an epoxide substituted with a trimethylammonium group.

Cationic cellulose copolymers or cellulose derivatives grafted with a water-soluble quaternary ammonium monomer are described especially in U.S. Pat. No. 4,131,576, and mention may be made of hydroxyalkylcelluloses, for instance hydroxymethyl-, hydroxyethyl- or hydroxypropylcelluloses grafted, in particular, with a [(meth)acrylic units] dimethyldiallylammonium salt. The commercial products corresponding to this definition are more particularly the products sold under the names CELQUAT L 200 and CELQUAT H 100 by the company National Starch.

The cationic galactomannan gums are described more particularly in U.S. Pat. Nos. 3,589,578 and 4,031, 307, and mention may be made of guar gums comprising cationic trialkylammonium groups.

Use is made, for example, of guar gums modified with a 2,3-epoxypropyltrimethylammonium salt (for example, chloride). Such products are especially sold under the names JAGUAR C13 S, JAGUAR C 15, JAGUAR C 17 or JAGUAR C162 by the company Rhodia.

(2) Polymers formed from piperazinyl units and divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers.

(3) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they comprise one or more tertiary amine functions, they can be quaternized.

(4) Polyamino amide derivatives resulting from the condensation of polyalkylene polyamines with polycarboxylic acids followed by alkylation with bifunctional agents. Mention may be made, for example, of adipic acid/dialkylaminohydroxyalkyl-dialkylenetriamine polymers in which the alkyl radical comprises from 1 to 4 carbon atoms and preferably denotes methyl, ethyl or propyl. Among these derivatives, mention may be made more particularly of the adipic acid/dimethylaminohydroxypropyl/diethylenetriamine polymers sold under the name CARTARETINE F, F4 or F8 by the company Sandoz.

(5) Polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms; the mole ratio between the polyalkylene polyamine and the dicarboxylic acid preferably being between 0.8:1 and 1.4:1; the resulting polyamino amide being reacted with epichlorohydrin in a mole ratio of epichlorohydrin relative to the secondary amine group of the polyamino amide preferably of between 0.5:1 and 1.8:1. Polymers of this type are sold in particular under the name HERCOSETT 57 by the company Hercules Inc. or alternatively under the name PD 170 or DELSETTE 101 by the company Hercules in the case of the adipic acid/epoxypropyl/diethylenetriamine copolymer.

(6) Cyclopolymers of alkyldiallylamine or of dialkyldiallylammonium, such as the homopolymers or copolymers containing, as main constituent of the chain, units corresponding to formula (XXX) or (XXXI):

(XXX)

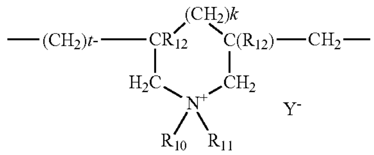

(XXXI)

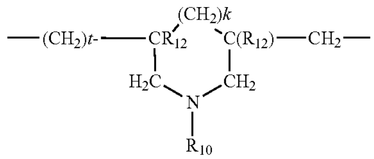

in which:

k and t are equal to 0 or 1, the sum k+t being equal to 1;

$R_{12}$ denotes a hydrogen atom or a methyl radical;

$R_{10}$ and $R_{11}$, independently of each other, denote a $C_1$-$C_6$ alkyl group, a hydroxyl($C_1$-$C_5$)alkyl group, a $C_1$-$C_4$ amidoalkyl group; or alternatively $R_{10}$ and $R_{11}$ may denote, together with the nitrogen atom to which they are attached, an heterocyclic group such as piperidinyl or morpholinyl; $R_{10}$ and $R_{11}$, independently of each other, preferably denote a $C_1$-$C_4$ alkyl group; and $Y^-$ is an anion such as bromide, chloride, acetate, borate, citrate, tartrate, bisulfate, bisulfite, sulfate or phosphate.

Mention may be made more particularly of the dimethyldiallylammonium salt (for example chloride) homopolymer sold for example under the name MERQUAT 100 by the company Nalco.

(7) Quaternary diammonium polymers comprising repeating units of formula:

(XXXII)

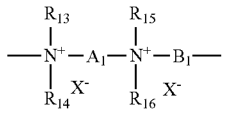

in which:

$R_{13}$, $R_{14}$, $R_{15}$ and $R_{16}$, which may be identical or different, represent aliphatic, alicyclic or arylaliphatic radicals comprising from 1 to 20 carbon atoms, or $C_1$-$C_{12}$ hydroxyalkylaliphatic radicals, or else $R_{13}$, $R_{14}$, $R_{15}$ and $R_{16}$, together or separately, constitute, with the nitrogen atoms to which they are attached, heterocycles optionally comprising a second non-nitrogen heteroatom, or else $R_{13}$, $R_{14}$, $R_{15}$ and $R_{16}$ represent a linear or branched $C_1$-$C_6$ alkyl radical substituted with a nitrile, ester, acyl, amide or —CO—O—$R_{17}$-D or —CO—NH—$R_{17}$-D group in which $R_{17}$ is an alkylene and D is a quaternary ammonium group;

A1 and B1 represent divalent polymethylene groups comprising from 2 to 20 carbon atoms, linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;

it being understood that A1, $R_{13}$ and $R_{15}$ can form, with the two nitrogen atoms to which they are attached, a piperazine ring;

in addition, if A1 denotes a linear or branched, saturated or unsaturated alkylene or hydroxyalkylene radical, B1 may also denote a group $(CH_2)_n$—CO-D-OC—$(CH_2)_p$— wherein n and p, which may be identical or different, denote an integer from 2 to 20, and wherein D denotes:

a) a glycol residue of formula —O—Z—O—, in which Z denotes a linear or branched hydrocarbon-based radical, or a group corresponding to one of the following formulae: —$(CH_2—CH_2—O)_x$—$CH_2$—$CH_2$— and —$[CH_2—CH(CH_3)—O]_y$—$CH_2$—$CH(CH_3)$—, where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or else the divalent radical —$CH_2$—$CH_2$—S—S—$CH_2$—$CH_2$—;

d) a ureylene group of formula: —NH—CO—NH—;

Preferably, $X^-$ is an anion such as chloride or bromide. These polymers have a number-average molar mass (Mn) generally of between 1000 and 100000.

Mention may be made more particularly of polymers that are composed of repeating units corresponding to the formula:

(XXXIII)

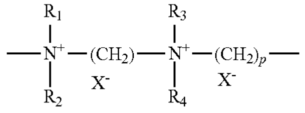

in which $R_1$, $R_2$, $R_3$ and $R_4$, which may be identical or different, denote an alkyl or hydroxyalkyl radical containing from 1 to 4 carbon atoms, n and p are integers ranging from 2 to 20, and $X^-$ is an anion derived from an organic or mineral acid.

A particularly preferred compound of formula (XXXIII) is that for which $R_1$, $R_2$, $R_3$ and $R_4$ represent a methyl radical and n=3, p=6 and X=C, known as Hexadimethrine chloride according to the INCI (CTFA) nomenclature.

(8) Polyquaternary ammonium polymers comprising units of formula (XXXIV):

(XXXIV)

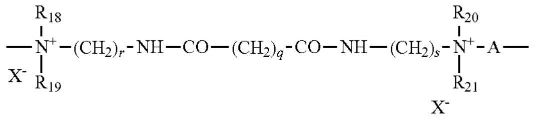

in which:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —$CH_2CH_2(OCH_2CH_2)_pOH$ group, in which p is equal to 0 or to an integer between 1 and 6, with the proviso that $R_{18}$, $R_{19}$, $R_{20}$ and $R_{21}$ do not simultaneously represent a hydrogen atom, r and s, which may be identical or different, are integers between 1 and 6, q is equal to 0 or to an integer between 1 and 34, $X^-$ denotes an anion such as a halide, A denotes a dihalide radical or preferably represents —$CH_2$—$CH_2$—O—$CH_2$—$CH_2$—.

Examples that may be mentioned include the products Mirapol® A15, Mirapol® AD1, Mirapol® AZ1 and Mirapol® 175 sold by the company Miranol.

(9) Quaternary polymers of vinylpyrrolidone and of vinylimidazole, for instance the products sold under the names Luviquat® FC 905, FC 550 and FC 370 by the company BASF.

(10) Polyamines such as Polyquart® H sold by Cognis, referred to under the name Polyethylene glycol (15) tallow polyamine in the CTFA dictionary.

(11) Polymers comprising in their structure:

(a) one or more units corresponding to formula (A) below:

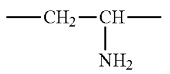

(A)

(b) optionally, one or more units corresponding to formula (B) below:

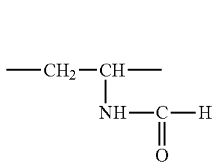

(B)

In other words, these polymers may be chosen especially from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to formula (A) and from 0 to 95 mol % of units corresponding to formula (B), preferentially from 10 mol % to 100 mol % of units corresponding to formula (A) and from 0 to 90 mol % of units corresponding to formula (B).

These polymers may be obtained, for example, by partial hydrolysis of polyvinylformamide. This hydrolysis may be performed in an acidic or basic medium.

The weight-average molecular mass of the said polymer, measured by light scattering, may range from 1,000 to 3000000 g/mol, preferably from 10,000 to 1,000,000 g/mol and more particularly from 100,000 to 500,000 g/mol.

The polymers comprising units of formula (A) and optionally units of formula (B) are sold especially under the name Lupamin by the company BASF, for instance, and in a non-limiting manner, the products sold under the names Lupamin 9095, Lupamin 5095, Lupamin 1095, Lupamin 9030 (or Luviquat 9030) and Lupamin 9010.

Other additional cationic polymers that may be used in the context of the invention are cationic proteins or cationic protein hydrolysates, polyalkyleneimines, in particular polyethyleneimines, polymers comprising vinylpyridine or vinylpyridinium units, condensates of polyamines and of epichlorohydrin, quaternary polyureylenes and chitin derivatives.

The additional cationic polymers, different from the cationic/amphoteric polymers comprising one or more acrylic and/or methacrylic units described above, are preferably chosen from the cationic polysaccharides corresponding to the general family (1).

More preferentially the additional cationic polymers are chosen from cationic guar gums comprising trialkylammonium groups (preferably $C_1$-$C_6$ alkyl groups, and more preferentially methyl groups), better still from hydroxyl($C_1$-$C_4$)alkyl guar gums comprising trialkylammonium groups, and even more preferably the additional cationic polymers are chosen from guar hydroxypropyltrimonium chlorides.

According to a preferred embodiment of the present invention, the composition can comprise:

- one or more polymer(s) comprising one or more cationic or quaternized (meth)acrylamide units, preferably chosen from (meth)acrylamido($C_1$-$C_6$ alkyl)tri($C_1$-$C_4$ alkyl) ammonium halide/(meth)acrylamide copolymers, (meth)acrylamido($C_1$-$C_6$ alkyl)tri($C_1$-$C_4$ alkyl) ammonium halide/(meth)acrylamide/(meth)acrylic acid terpolymers, (meth)acrylamido($C_1$-$C_6$ alkyl)tri ($C_1$-$C_4$ alkyl) ammonium halide/($C_1$-$C_6$ alkyl) (meth) acrylate/(meth)acrylic acid terpolymers; and mixtures thereof, and
- one or more additional cationic polymers, different from the polymers comprising one or more cationic or quaternized (meth)acrylamide units described above, preferably chosen from the cationic polysaccharides corresponding to the general family (1); more preferentially chosen from cationic guar gums comprising trialkylammonium groups; better still from hydroxyalkyl guar gums comprising trialkylammonium groups; and even more preferably the additional polymers are chosen from guar hydroxypropyltrimonium chlorides.

The amount of additional cationic polymer(s), different from the polymers comprising one or more cationic or quaternized (meth)acrylamide units, when they are present in the cosmetic composition of the present invention, preferably ranges from 0.01 to 10% by weight, more preferentially from 0.02 to 5% by weight, and better still from 0.05 to 2% by weight, and even more preferably 0.1 to 1% by weight relative to the total weight of the cosmetic composition.

Optional Additive(s)

The cosmetic composition of the invention may also contain various additives conventionally used in hair compositions.

As additives that may be used in accordance with the invention, mention may be made of anionic or non-ionic polymers, additional amphoteric polymers different from the polymers comprising one or more cationic or quaternized (meth)acrylamide units previously described, antidandruff agents, anti-seborrhoea agents, agents for preventing hair loss and/or for promoting hair regrowth, fatty substances, vitamins and provitamins including panthenol, sunscreens, mineral or organic pigments, sequestrants, plasticizers, solubilizers, acidifying agents, mineral or organic thickeners, especially polymeric thickeners, opacifiers or nacreous agents, antioxidants, hydroxy acids, fragrances and preserving agents, and mixtures thereof.

The above additives are generally present in an amount for each of them of between 0.01% and 40% by weight, and preferably between 0.1% and 20% by weight relative to the weight of the cosmetic composition of the invention.

Needless to say, a person skilled in the art will take care to select this or these optional additive(s) such that the advantageous properties intrinsically associated with the cosmetic composition in accordance with the invention are not, or are not substantially, adversely affected by the envisaged addition(s).

The present invention also relates to a cosmetic treatment process, in particular for washing and/or conditioning keratin fibres, which consists in applying to the said keratin fibres a composition as described above, and after an optional leave-on time, optionally removing it by rinsing.

The leave-on time of the composition on the keratin fibres may range from a few seconds to 15 minutes, better still from 5 seconds to 10 minutes and even better still from 10 seconds to 5 minutes.

The composition may be applied to wet or dry keratin fibres.

The composition could be a shampoo or a conditioner,

Finally, the present invention relates to the use of a composition as described above for washing and/or conditioning keratin fibres.

In the present invention, the term "keratin fibres" denotes human keratin fibres, and in particular human hair such as hair.

In the above description, all the preferred embodiments with regard to the components may be used individually or in combination.

The examples that follow serve to illustrate the invention.

EXAMPLES

In the examples that follow and unless otherwise indicated, the amounts are given as weight percentages of active material (AM) relative to the total weight of the composition.

Example 1: Preparation of an Oil-In-Water Emulsion 450 g of amino silicone fluid (trimethylsilyl-terminated aminoethyl-aminopropylmethylsiloxane-dimethylsiloxane copolymer with amine value of 7.2 mg of KOH/g sample, and a viscosity of 5,600 mPa·s at 25° C.) were introduced in an emulsion tank. Stirring was started and 1,800 g of trimethylsilyl terminated dimethylsiloxane polymer fluid of viscosity 61,500 mPa·s at 25° C. were introduced under stirring in the same tank. Both fluids were mixed for 2 hours at room temperature.

In a separate tank, 49 g of steareth-6 and 62 g of PEG-100 stearate were introduced and heated to 60° C. The temperature was maintained till both emulsifiers became liquid. Then 31 g of trideceth-3 and 350 g of trideceth-10 (80% of active material) were added. These nonionic emulsifiers mixture had an HLB value=11.25.

Then 80 g water and 6.2 g glacial acetic acid were added to the tank and the mixing started. The mixing was continued till whole mass became a creamy paste. The whole paste was introduced in the emulsion tank. Homogenization was carried out for 30 minutes at room temperature. 79.6 g demineralized water were added and homogenization was carried out for 60 minutes. 72.7 g demineralized water were added and homogenization was carried out for 50 minutes. 197.4 g demineralized water were added and homogenization was carried out for 5 minutes. 294.3 g demineralized water were added and homogenization was carried out for 5 minutes. 180 g demineralized water were added and homogenization was carried out for 5 minutes. 180 g demineralized water were added and homogenization was carried out for 5 minutes. 197.4 g demineralized water were added and homogenization was carried out for 5 minutes. 197.4 g demineralized water were added and homogenize for 3 minutes. 228.5 g demineralized water were added and homogenization was carried out for 3 minutes. Lastly 40.5 g 2-phenoxyethanol were added as a biocide and homogenization was carried out for 3 minutes.

A stable oil-in-water emulsion having D50 particle size of 170 nm was obtained.

Example 2

The following compositions 1 and 2 and comparative composition 1' were prepared from the ingredients indicated in table 1 below (wt. % of AM).

TABLE 1

| Composition | 1 (Invention) | 2 (Invention) | 1' (Comparative) |
|---|---|---|---|
| Coco-betaine | 1.8 | 0.3 | 1.8 |
| Sodium laureth sulfate | 13.9 | 13.9 | 13.9 |
| Sodium chloride | 1.5 | 1.036 | 1.5 |
| Carbomer | — | 0.2 | — |
| Acrylamidopropyltrimonium chloride/acrylamide copolymer (=APTAC/AA) | 0.15 | 0.15 | — |
| diallyldimethylammonium/ acrylamide copolymer (Polyquaternium-7) | — | — | 0.15 |
| Dimethicone (and) Amodimethicone (and) Trideceth-10 (and) PEG-100 stearate (and) Steareth-6 (and) Trideceth-3 (of exemple 1) | 4 % of emulsion, i.e. 0.4% AM SiA + 1.6% AM of Si | 4% of emulsion, i.e. 0.4% AM SiA + 1.6% AM of Si | 4% of emulsion, i.e. 0.4% AM SiA + 1.6% AM of Si |
| Glycerin | — | 0.5 | — |
| Cocamidopropyl betaine | — | 1.22 | — |
| Cocos nucifera (coconut) oil/cocos nucifera oil | — | 0.02 | — |
| Hexylene glycol | — | 0.15 | — |
| Glycol distearate | — | 1.59 | — |
| PPG-5-ceteth-20 | 0.1 | — | 0.1 |
| Propylene glycol (and) PEG-55 propylene glycol oleate | 0.16 + 0.16 | — | 0.16 + 0.16 |
| Preservatives, pH agent | qs | qs | qs |
| Water Qs | 100 | 100 | 100 |

*AM = active material
SiA: amodimethicone
Si: PDMS

The compositions could be used as a shampoo.

The compositions were applied to the hair. A significantly improved disentangling was obtained in particular with composition 1 according to the invention, relative to comparative composition 1'.

Then each composition 1 and 1' was applied 5 times on hair locks with a rinsing step after each application, and the silicone deposition was measured by a WDXRF Optim'x Thermofischer (Wavelength Dispersion) XRF system on samples of 250 mg of hair. This measurement has been made after one application and after 5 applications for each composition.

The quantities of silicone deposited are indicated in table 2 below, in µg/g of hair.

TABLE 2

| | | Composition 1 | Composition 1' |
|---|---|---|---|
| Application No | 1 | 2,276 ± 18 | 746 ± 8 |
| | 5 | 8,289 ± 32 | 2,065 ± 16 |

Table 2 shows that the use of the polymer of the invention results in a significantly improved quantity of silicone deposited on hair.

Example 3

The following conditioners have been prepared from the ingredients indicated in table 3 below (wt. % of AM).

TABLE 3

| | 2' (Comparative) | 3 (Invention) | 4 (Invention) |
|---|---|---|---|
| Behentrimonium chloride | 0.474 | 0.474 | 0.474 |
| Polyglycerin-10 | 0.012 | 0.012 | — |
| Dimethicone (and) Amodimethicone (and) Trideceth-10 (and) PEG-100 stearate (and) Steareth-6 (and) Trideceth-3 of example 1 | 8% of emulsion (0.8% of SiA and 3.2% of Si) | 8% of emulsion (0.8% of SiA and 3.2% of Si) | 8% of emulsion (0.8% of SiA and 3.2% of Si) |
| Cetyl esters | 0.8 | 0.8 | 0.8 |
| Charcoal powder | 0.1 | 0.1 | — |
| Cetrimonium chloride | 0.625 | 0.625 | 0.625 |
| Iron oxides | 1 | 1 | 0.25 |
| RED 33 | 0.01 | 0.01 | 0.01 |
| Cetyl alcohol | 4 | 4 | 4 |
| BLUE 1 | 0.06 | 0.06 | 0.06 |
| EXT. VIOLET 2 | 0.044 | 0.044 | 0.044 |
| ORANGE 4 | 0.076 | 0.076 | 0.076 |
| Isopropyl alcohol | 0.108 | 0.108 | 0.108 |
| Cetearyl alcohol | 0.7 | 0.7 | 0.7 |
| Polyglyceryl-10 stearate | 0.012 | 0.012 | — |
| Polyglyceryl-10 myristate | 0.012 | 0.012 | — |
| Hydroxyethylcellulose | 0.25 | 0.25 | — |
| Dipalmitoylethyl hydroxyethylmonium methosulfate | 0.3 | 0.3 | 0.3 |
| Acrylamidopropyl-trimonium chloride/acrylamide copolymer | | 0.225 | 0.225 |
| Isododecane | — | — | 0.6 |
| Acrylates/polytrimethyl-siloxymethacrylate copolymer | — | — | 0.4 |

TABLE 3-continued

| | 2' (Comparative) | 3 (Invention) | 4 (Invention) |
|---|---|---|---|
| Mica | — | — | 0.04075 |
| Preservatives, fragrance | qs | qs | qs |
| Water qs | 100 | 100 | 100 |

SiA: amodimethicone

Si: PDMS

Compositions 2' and 3 were each applied to locks of hair, in a proportion of 0.4 g per gram of lock. The locks were then rinsed with water and dried under a hood (60° C.).

The color of each lock was then evaluated in the CIE L* a* b* system, using a Minolta Spectrophotometer CM2600D colorimeter.

In this L* a* b* system, the three parameters respectively denote the intensity of the color (L*), the green/red color axis (a*) and the blue/yellow color axis (b*).

The variation in the coloration of the locks before and after dyeing (i.e. application of the tested composition) is measured by ($\Delta E_{ab}*$) which corresponds to the color uptake according to the following equation:

$$\Delta E_{ab}*=\sqrt{(L*-L_0*)^2+(a*=a_0*)^2+(b*-b_0)^2}$$

In this equation, L*, a* and b* represent the values measured after dyeing with composition 2' (comparative) or 3 (invention) and $L_0$*, $a_0$* and $b_0$* represent the values measured before dyeing, corresponding to an untreated control lock (50% grey hair).

The greater the $\Delta E_{ab}$* value, the greater the difference in color of the lock before and after dyeing, which shows good colour uptake.

The results are indicated in the table 4 below.

TABLE 4

| Composition | $\Delta E_{ab}$* (D65) |
|---|---|
| 2' (comparative) | 4.34 |
| 3 (invention) | 5.87 |

Table 4 shows that the use of the polymer of the invention results in an improved good colour uptake.

The invention claimed is:

1. A cosmetic composition, comprising:

(a) from 0.04% to 1% of at least one polymer comprising one or more cationic or quaternized acrylamide and/or methacrylamide units;

(b) from 0.5% to 10% of an oil-in-water emulsion comprising:

a silicone mixture comprising:

(i) at least one trialkylsilyl-terminated dialkylpolysiloxane having a viscosity ranging from 40,000 to less than 100,000 mPa·s at 25° C., and (ii) at least one amino silicone having a viscosity ranging from 1,000 to 15,000 mPa·s at 25° C. and an amine value ranging from 2 to 10 mg of KOH per gram of amino silicone, a mixture of at least two emulsifiers, wherein:

the mixture of emulsifiers comprises at least one nonionic emulsifier, and the mixture of emulsifiers has an HLB value ranging from 10 to 16, and water, wherein the oil-in-water emulsion has a D50 particle size of less than 350 nm; and (c) from 1% to 25% of at least one surfactant, wherein the at least one polymer (a) is chosen from:

(meth)acrylamido ($C_1$-$C_6$ alkyl)tri($C_1$-$C_4$ alkyl) ammonium halide/(meth)acrylamide copolymers, (meth)acrylamido ($C_1$-$C_6$ alkyl)tri($C_1$-$C_4$ alkyl) ammonium halide/(meth)acrylamide/(meth)acrylic acid terpolymers, (meth)acrylamido ($C_1$-$C_6$ alkyl)tri($C_1$-$C_4$ alkyl) ammonium halide/($C_1$-$C_6$ alkyl) (meth)acrylate/(meth) acrylic acid terpolymers, or mixtures thereof, wherein all amounts are by weight, relative to the total weight of the composition.

2. The cosmetic composition according to claim 1, comprising at least one polymer (a) chosen from:

acrylamidopropyltrimethylammonium chloride/acrylamide copolymers, acrylamide/methacrylamidopropyltrimethylammonium chloride/acrylic acid terpolymers, acrylic acid/methylacrylamidopropyltrimethylammonium chloride/methyl acrylates terpolymers, or mixtures thereof.

3. The cosmetic composition according to claim 1, wherein the total amount of polymers (a) ranges from 0.05% to 0.5% by weight, relative to the total weight of the composition.

4. The cosmetic composition according to claim 1, wherein the composition comprises at least one trialkylsilyl-terminated dialkylpolysiloxane chosen from compounds of formula (IX):

(IX)

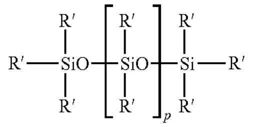

wherein:

R' is independently chosen from monovalent hydrocarbon radicals having from 1 to 18 carbon atoms, and p is an integer ranging from 500 to 2,000.

5. The cosmetic composition according to claim 1, wherein the composition comprises at least one amino silicone chosen from compounds of formula (X):

(X)

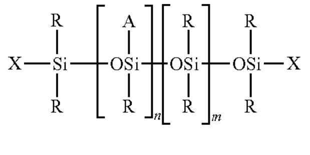

wherein:

R is independently chosen from monovalent hydrocarbon radicals having from 1 to 18 carbon atoms;

X is independently chosen from R or a hydroxyl (—OH) or a $C_1$-$C_6$ alkoxy group;

A is an amino radical of the following formula, or a protonated amino form thereof:

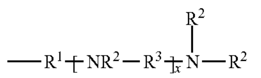

wherein $R^1$ is a $C_1$-$C_6$ alkylene radical, $R^2$ is independently chosen from a hydrogen atom or a $C_1$-$C_4$ alkyl radical, $R^3$ is a $C_1$-$C_6$-alkylene radical, and x is 0 or 1; and the sum of m+n is an integer from 50 to about 1000.

6. The cosmetic composition according to claim 1, wherein the silicone mixture comprises:

(i) from 70 to 90% by weight of trialkylsilyl terminated dialkylpolysiloxanes having a viscosity ranging from 40,000 to less than 100,000 mPa·s at 25° C., relative to the total weight of the silicone mixture, and (ii) from 10 to 30% by weight of amino silicones having a viscosity ranging from 1,000 to 15,000 mPa·s at 25° C. and an amine value ranging from 2 to 10 mg of KOH per gram of amino silicone, relative to the total weight of the silicone mixture.

7. The cosmetic composition according to claim 1, wherein the mixture of emulsifiers comprises at least one emulsifier chosen from:

(i) polyoxyalkylene alkyl ethers comprising (poly)ethoxylated fatty alcohols of the formula:

$$R_3—(OCH_2CH_2)_cOH$$

wherein:

$R_3$ is chosen from a linear or branched $C_8$-$C_{40}$ alkyl or alkenyl group, and c is an integer ranging from 1 to 200;

(ii) polyoxyalkylene ($C_8$-$C_{32}$) alkylphenyl ethers;

(iii) polyoxyalkylene sorbitan ($C_8$-$C_{32}$) fatty acid esters;

(iv) polyoxyethylenated ($C_8$-$C_{32}$) fatty acid esters containing from 2 to 150 mol of ethylene oxide; or (v) mixtures thereof.

8. The cosmetic composition according to claim 1, wherein, for the oil-in-water emulsion, wherein one or more of the following conditions are satisfied:

the total amount of emulsifiers ranges from 5 to 15% by weight, relative to the total weight of the emulsion;

the total amount of nonionic emulsifiers ranges from 5 to 15% by weight, relative to the total weight of the emulsion;

the total amount of cationic emulsifiers ranges from 0.5 to 1.5% by weight, relative to the total weight of the emulsion;

the silicone mixture is present in a total amount ranging from 40 to 60% by weight, relative to the total weight of the emulsion;

the total amount of trialkylsilyl terminated dialkylpolysiloxanes ranges from 35 to 45% by weight, relative to the total weight of the emulsion;

the total amount of amino silicones ranges from 5 to 15% by weight, relative to the total weight of the emulsion; and/or the total amount of water ranges from 25 to 50% by weight, relative to the total weight of the emulsion.

9. The cosmetic composition according to claim 1, wherein the oil-in-water emulsion has a D50 particle size ranging from 100 to 300 nm.

10. The cosmetic composition according to claim 1, wherein the oil-in-water emulsion is present in the composition in an amount ranging from 0.5% to 8% by weight, relative to the total weight of the composition.

11. The cosmetic composition according to claim 1, wherein the at least one surfactant (c) comprises at least one anionic surfactant.

12. The cosmetic composition according to claim 1, wherein the at least one surfactant (c) comprises at least one amphoteric surfactant, at least one zwitterionic surfactant, or a mixture thereof.

13. The cosmetic composition according to claim 1, further comprising at least one compound chosen from direct dyes, pigments, or mixtures thereof.

14. The cosmetic composition according to claim 13, wherein:

the total amount of direct dyes ranges from 0.001% to 10% by weight, relative to the total weight of the composition, and/or the total amount of pigments ranges from 0.01% to 15% by weight, relative to the total weight of the composition.

15. A cosmetic composition comprising:

(a) from 0.04% to 1% by weight, relative to the total weight of the composition, of at least one polymer chosen from acrylamidopropyltrimonium chloride/acrylamide copolymers, acrylamide/methacrylamidopropyltrimethylammonium chloride/acrylic acid terpolymers, acrylic acid/methylacrylamidopropyltrimethylammonium chloride/methyl acrylates terpolymers, or mixtures thereof;

(b) from 0.5% to 10% by weight, relative to the total weight of the composition, of an oil-in-water emulsion comprising:

from 40% to 60% by weight, relative to the total weight of the oil-in-water emulsion, of a silicone mixture comprising:

(i) from 75% to 85% by weight of at least one trialkylsilyl-terminated dialkylpolysiloxane having a viscosity ranging from 40,000 to less than 100,000 mPa·s at 25° C., relative to the total weight of the silicone mixture, and (ii) from 15% to 25% by weight of at least one amino silicone having a viscosity ranging from 1,500 to 15,000 mPa·s at 25° C. and an amine value ranging from 3.5 to 8 mg of KOH per gram of amino silicone, relative to the total weight of the silicone mixture, a mixture of at least two emulsifiers, wherein:

the mixture of emulsifiers comprises from 5% to 15% by weight, relative to the total weight of the oil-in-water emulsion, of nonionic emulsifiers, and the mixture of emulsifiers has an HLB value ranging from 10 to 16, and water, wherein the oil-in-water emulsion has a D50 particle size ranging from 100 nm to 300 nm; and (c) from 1% to 25% of at least one anionic surfactant, wherein all amounts are by weight, relative to the total weight of the composition.

16. A process for washing and/or conditioning keratin fibres comprising applying to the keratin fibres a composition comprising:

(a) from 0.04% to 1% of at least one polymer comprising one or more cationic or quaternized acrylamide and/or methacrylamide units;

(b) from 0.5% to 10% of an oil-in-water emulsion comprising:

a silicone mixture comprising:

(i) at least one trialkylsilyl-terminated dialkylpolysiloxane having a viscosity ranging from 40,000 to less than 100,000 mPa·s at 25° C., and (ii) at least one amino silicone having a viscosity ranging from 1,000 to 15,000 mPa·s at 25° C. and an amine value ranging from 2 to 10 mg of KOH per gram of amino silicone, a mixture of at least two emulsifiers, wherein:

the mixture of emulsifiers comprises at least one nonionic emulsifier, and the mixture of emulsifiers has an HLB value ranging from 10 to 16, and water, wherein the oil-in-water emulsion has a D50 particle size of less than 350 nm; and (c) from 1% to 25% of at least one surfactant, wherein the at least one polymer (a) is chosen from:

(meth)acrylamido (C1-C6 alkyl)tri(C1-C4 alkyl) ammonium halide/(meth)acrylamide copolymers, (meth)acrylamido (C1-C6 alkyl)tri(C1-C4 alkyl) ammonium halide/(meth)acrylamide/(meth) acrylic acid terpolymers, (meth)acrylamido (C1-C6 alkyl)tri(C1-C4 alkyl) ammonium halide/(C1-C6 alkyl) (meth) acrylate/(meth)acrylic acid terpolymers, or mixtures thereof, wherein all amounts are by weight, relative to the total weight of the composition.

* * * * *